US005329976A

United States Patent [19]

Haber et al.

[11] Patent Number: 5,329,976

[45] Date of Patent: Jul. 19, 1994

[54] SYRINGE-FILLING AND MEDICATION MIXING DISPENSER

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 948,278

[22] Filed: Sep. 21, 1992

Related U.S. Application Data

[63] Continuation-in-part of Ser. No. 805,503, Dec. 9, 1991.

[51] Int. Cl.[5] .......... A61M 1/00

[52] U.S. Cl. .......... 141/25; 141/309; 141/18; 141/35; 141/329; 604/411; 604/191; 604/407

[58] Field of Search .......... 141/18, 21, 25–27, 141/29, 46, 285, 309, 59, 35, 104–106, 329, 330, 375; 604/82, 86, 87, 205, 207–211, 232, 407, 411–415, 134–136, 139, 191; 222/135–137

[56] References Cited

U.S. PATENT DOCUMENTS

| | | | |
|---|---|---|---|
| 2,100,610 | 11/1937 | Paisley et al. | 141/329 |
| 3,425,414 | 2/1969 | La Roche . | |
| 3,853,158 | 12/1974 | Whitty . | |
| 3,932,136 | 1/1976 | Stickney . | |
| 3,935,883 | 2/1976 | Stach et al. | 141/27 |
| 4,253,501 | 3/1981 | Ogle | 141/27 |
| 4,296,785 | 10/1981 | Vitello et al. | 141/105 |
| 4,434,820 | 3/1984 | Glass | 141/2 |
| 4,505,709 | 3/1985 | Froning et al. | 604/411 |
| 4,666,430 | 5/1987 | Brown et al. | 222/136 X |
| 4,856,567 | 8/1989 | Cosmai | 604/411 |
| 4,877,065 | 10/1989 | Lamboy et al. | 141/18 |
| 4,998,570 | 3/1991 | Strong | 141/27 |
| 5,029,621 | 7/1991 | Lewis | 141/59 X |
| 5,037,390 | 8/1991 | Raines et al. | 604/411 |
| 5,104,624 | 4/1992 | Labriola | 141/25 X |
| 5,137,516 | 8/1992 | Rand et al. | 604/136 |

FOREIGN PATENT DOCUMENTS

WO90/07531 7/1990 PCT Int'l Appl. .

*Primary Examiner*—J. Casimer Jacyna
*Attorney, Agent, or Firm*—Townsend & Townsend Khourie & Crew

[57] ABSTRACT

A medication dispenser (2, 120) is used to directly fill a syringe (8, 134) with measured amounts of one or more liquid medications, typically two different types of insulin, from containers, such as vials (4, 6) and cartridges (230, 232, 234) each having a septum at one end; each cartridge has a pierceable piston (256) at the other end. The septum of each container is pierced by hollow liquid spikes (54) while hollow gas spikes (56) pierce the septum of the vial and the piston of the cartridge. Liquid is pumped out of the container and air is replaced into the container through the liquid and gas spikes. Two of the cartridges can contain a diluent (231) and a lyophilized component (233) respectively; the diluent in the first cartridge can be pumped into the second cartridge through a one-way valve to create a mixed pharmaceutical which is then pumped into the syringe, with or without another pharmaceutical.

22 Claims, 22 Drawing Sheets

SYRINGE-FILLING AND MEDICATION MIXING DISPENSER

CROSS REFERENCE TO RELATED APPLICATIONS

This is a continuation-in-part of U.S. patent application Ser. No. 07/805,503 filed Dec. 9, 1991 for Syringe-Filling Medication Dispenser, the disclosure of which is incorporated by reference. This is also related to U.S. Pat. application Ser. No. 07/667,319 filed Mar. 8, 1991 for Multiple Cartridge Syringe; and U.S. patent application Ser. No. 07/668,278 filed Mar. 8, 1991 for Multi-pharmaceutical Syringe, all assigned to the assignee of the present invention, the disclosures of which are incorporated by reference.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake and expected activity. For example, insulin injected at the beginning of an active day may have more of the fast-acting insulin, while the insulin injection given at the end of the day before going to bed would likely have more intermediate or long-acting insulin.

One of the problems with conventional insulin syringes is that they are designed to inject only one type of insulin, not a combination. Although insulin can be obtained as a mixture of the two types, the mixtures are generally a preset combination, such as 70% intermediate-acting and 30% fast-acting. Thus, the prior art limits the insulin user to a set mixture of the two insulins or the need to make two separate injections.

Another problem relates to pharmaceuticals which are kept in a lyophilized (dried) condition until use; they are then mixed with a diluent to reconstitute the pharmaceutical. This is conventionally done by syringe transfer.

SUMMARY OF THE INVENTION

The present invention is directed to a medication dispenser which can be used with one or more conventional medication containing containers, such as vials or cartridges, to supply a conventional syringe with a desired amount of the one or more medications. This permits the user to deliver medication, such as insulin, in desired amounts and proportions of each from a single, typically conventional, syringe. The dispenser also permits reconstituting a lyophilized pharmaceutical by mixing two or more pharmaceutical components prior to supplying the syringe with the medication.

The medication dispenser is typically used to directly fill a syringe with measured amounts of one or more liquid medications. The dispenser includes a body which has a number of cavities which are used to hold or position two or more liquid medication containers, typically vials or cartridges, and a syringe. The vials and cartridges are of the type having a septum at one end. The septum of each vial is pierced by a pair of hollow spikes. One of the spikes, the liquid spike, is used to allow the liquid medication to flow out of the vial while the other spike, the gas spike, is used to introduce air into the vial to replace the liquid medication drawn from the vial. With cartridge, the liquid spike pierces the septum while the gas spike pierces an elastomeric piston at the other end of the cartridge. Measured amounts of the liquid medication are pumped out of each vial while air simultaneously replaces the liquid pumped out of the vial. The replacement can be either passive, in which the act of pumping liquid medication through the liquid spike causes air to be pulled into the vial, or active, by which air is pumped into the vial at the same rate as liquid is pumped out of the vial.

The present invention finds particular utility for use in dispensing two different types of insulin into a syringe; this use is described with reference to the preferred embodiments. However, the invention could be used with a single medication as well. For example, human growth hormone is very expensive and requires accurate doses. With the present invention, two vials of human growth hormone could be mounted to the dispenser; when one vial is completely drained, the other vial could be used to keep from wasting the last bit of the growth hormone in the one vial. Also, the invention could be carried out using a dispenser usable with one medication container or three or more medication containers. In addition, one or more of the containers could contain a lyophilized pharmaceutical and another a diluent. The two could be connected so the user could reconstitute the lyophilized pharmaceutical just prior to use.

The liquid can be pumped using different types of pumps. One pump type is a reciprocating piston and cylinder type pump. With the reciprocating pump, the piston is reciprocated within the cylinder a desired number of times according to how much medicine is to be driven into the syringe. The dispenser is constructed to prevent the reverse flow of liquid into the pharmaceutical containers. For example, with a reciprocating pump-type of dispenser, check valves can be used. Other types of dispensers, such as one using a peristaltic pump, can prevent reverse flow through the construction of the pump itself. The invention permits insulin users the freedom to quickly and easily select the proportions of insulin to be injected depending upon the user's current needs.

One of the primary advantages of the invention is that it is designed to be used with conventional syringes and conventional medication-containing cartridges and vials. Each of the disclosed embodiments of the invention permits the user to select the amount of one or more medications to be dispensed into a syringe through the syringe's needle cannula. The invention provides flexibility and ease of use with a relatively inexpensive dispenser.

With the present invention, the inside of the vial remains at essentially atmospheric pressure. The gas used to replace the liquid drawn out of the vial is typically air; however, other gases such as nitrogen could be used as well.

The needle cannula typically provides a relatively narrow restriction for the passage of the liquid medication. The present invention recognizes that this restriction exists and accommodates it through the construction of the fluid path between the pump and the needle cannula. With the peristaltic pump version, the hollow tubes which couple the peristaltic pump to the common fluid chamber adjacent the needle cannula are constructed so that they can expand or bulge to accommodate intermittently high flow rates by providing a resilient reservoir or chamber leading into the needle cannula. With the reciprocating pump embodiment, the flow path is partially defined by a resilient surface which can be deformed when under pressure thus enlarging the volume of the flow path to accommodate the sudden increase in the volume of liquid medication from the reciprocating pump.

Other features and advantages of the invention will appear from the following description in which the preferred embodiments have been set forth in detail in conjunction with the accompanying drawings.

DESCRIPTION OF THE PREFERRED EMBODIMENT

Figure 1:
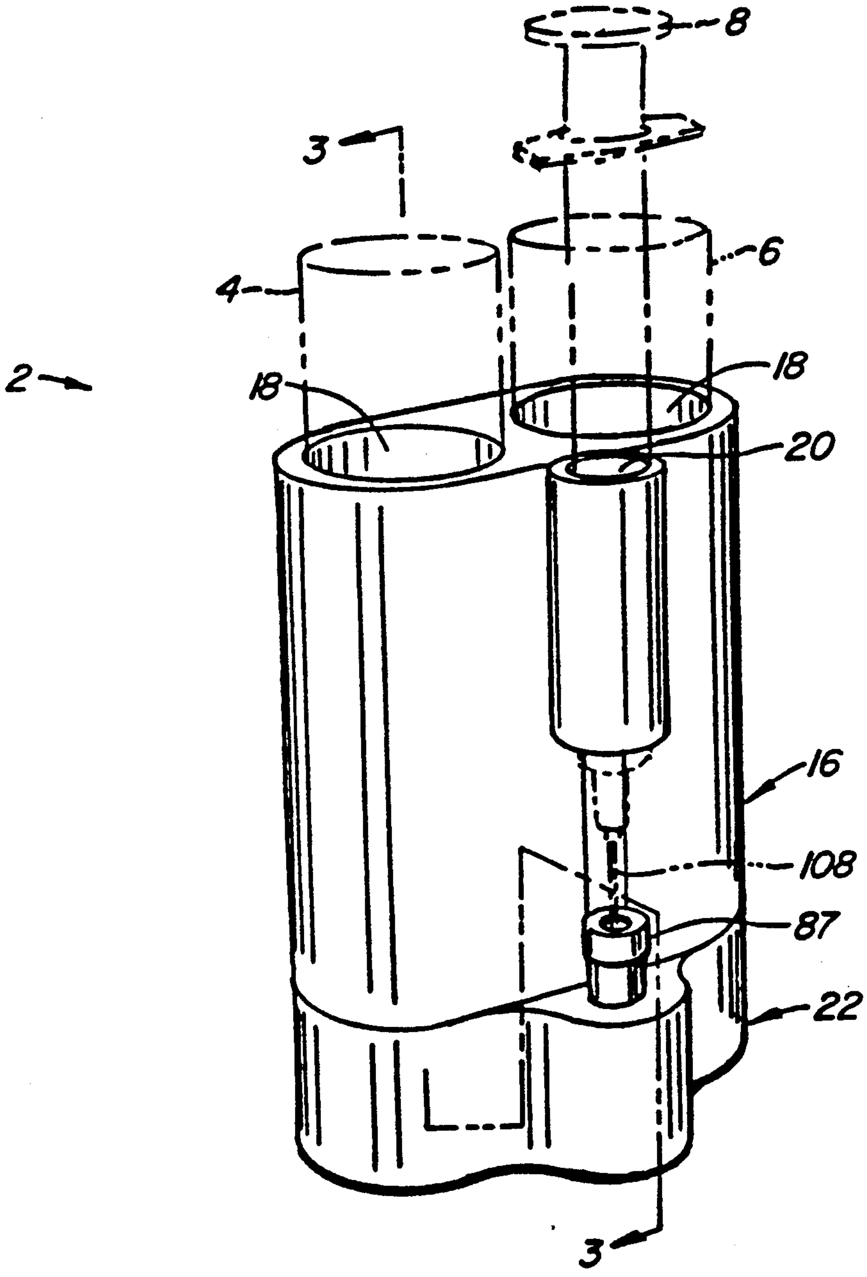
FIG. 1 is a perspective view of a reciprocating pump embodiment of a multiple medication dispenser made according to the invention with first and second vials and a syringe shown in phantom lines.
Figure 2:
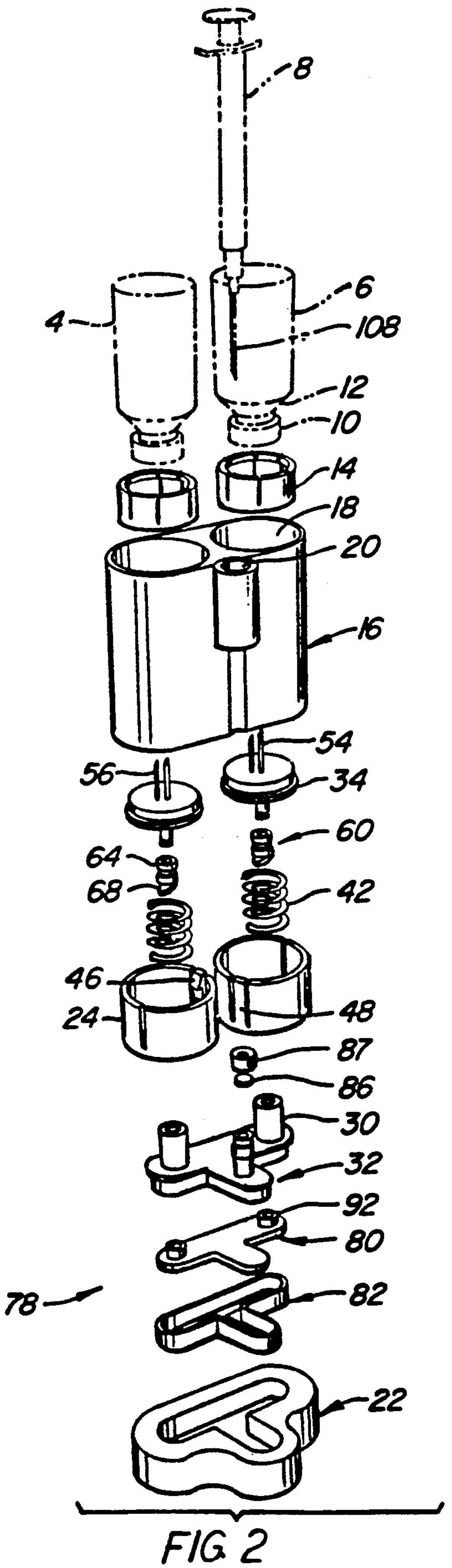
FIG. 2 is an exploded isometric view of the dispenser of FIG. 1.

FIGS. 1 and 2 illustrate a first reciprocating pump type multiple medication dispenser for use with first and second vials 4, 6 and a syringe 8. The following description will discuss first vial 4 and the various components associated therewith recognizing that similar components will be present and used with second vial 6 but not described independently; this is clearly illustrated in FIG. 2. Vial 4 is of the type having a pierceable septum, not shown, held in place by a band 10 at the access end 12 of vial 4. A segmented adaptor ring 14 is mounted to vial 4 at access end 12 for the reasons described below. By the use of adaptor ring 14, different types and configurations of vials 4 can be used with only the need to change adaptor ring 14.

Dispenser 2 also includes a body 16 having vial guide bores 18 and a syringe guide bore 20. Body 16 rests on, but is freely removable from, a support base 22 as shown in FIG. 1.

Figure 3:
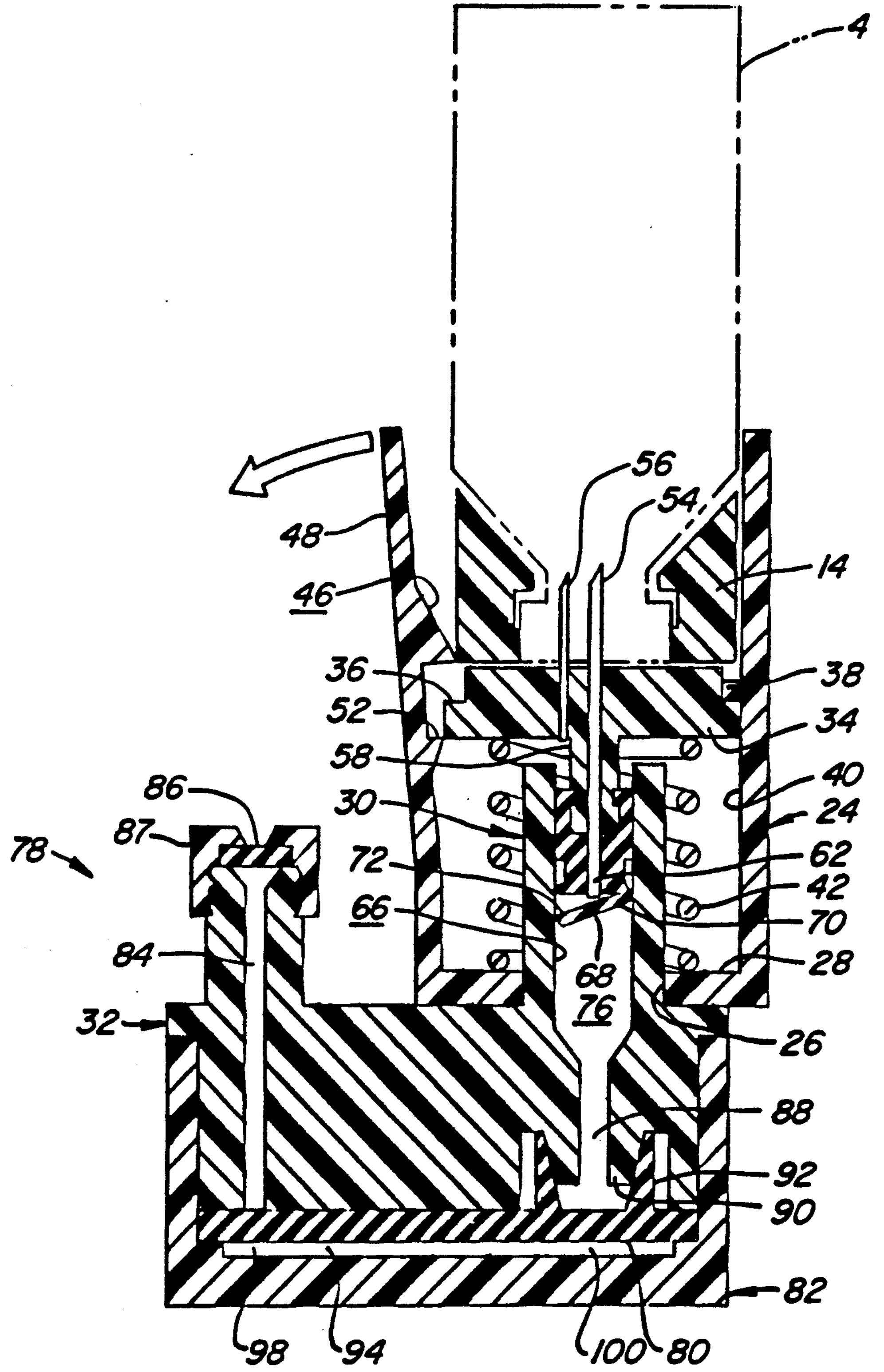
FIG. 3 is a cross-sectional view taken along line 3—3 of FIG. 1 but omitting the body and the support base.

FIG. 3 illustrates the structure of FIG. 1 as viewed along line 3-3 but with body 16 and support base 22 not illustrated. Dispenser 2 includes a pair of cup-shaped split guide rings 24 each having a central opening 26 at the base 28 of guide ring 24. Opening 26 is sized to fit snugly around a cylinder 30 extending upwardly as a one piece extension from a manifold cover 32. Adaptor ring 14, body 16, split guide ring 24, cylinder 30 and manifold cover 32 are all typically made of a hard plastic, such as polycarbonate. Split guide ring 24 is secured to manifold cover 32 using an adhesive, by ultrasonic welding or by other appropriate techniques.

A disk-like spike support 34 is movably mounted within each split guide ring 24. Spike support 34 has an annular ledge 36 which presses against a lug 38 extending inwardly from the inner wall 40 of split guide ring 24 by the force of a coil compression spring 42, typically made of spring-quality stainless steel. As suggested in FIGS. 4 and 5, movement of vial 4 together with adaptor ring 14 in the direction of arrow 44 causes ring 14 to engage camming surface 46 extending from the inside of resilient arm 48 in the direction of arrow 50. Doing so permits spike support 34 to disengage from an upwardly facing ledge 52 formed on the inside of arm 48 below surface 46. This permits spike support 34 to move downwardly, in the direction of arrow 44, as discussed below.

Figure 4:
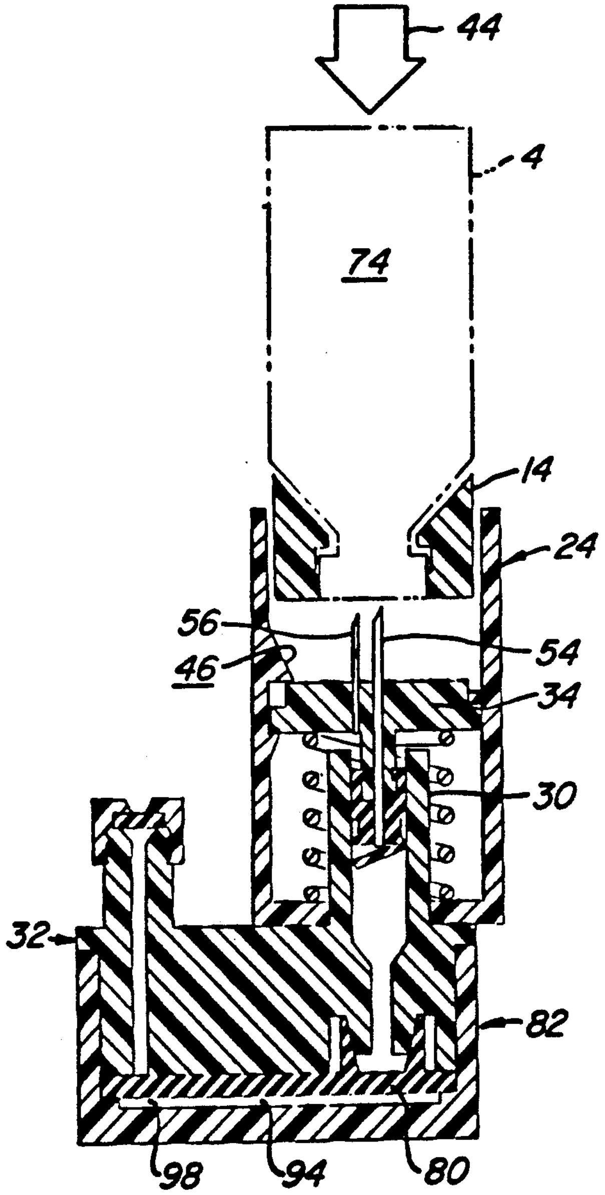
FIG. 4 shows the structure of FIG. 3 just prior to mounting a vial, to which an adaptor ring has been mounted, into the split ring guide.
Figure 5:
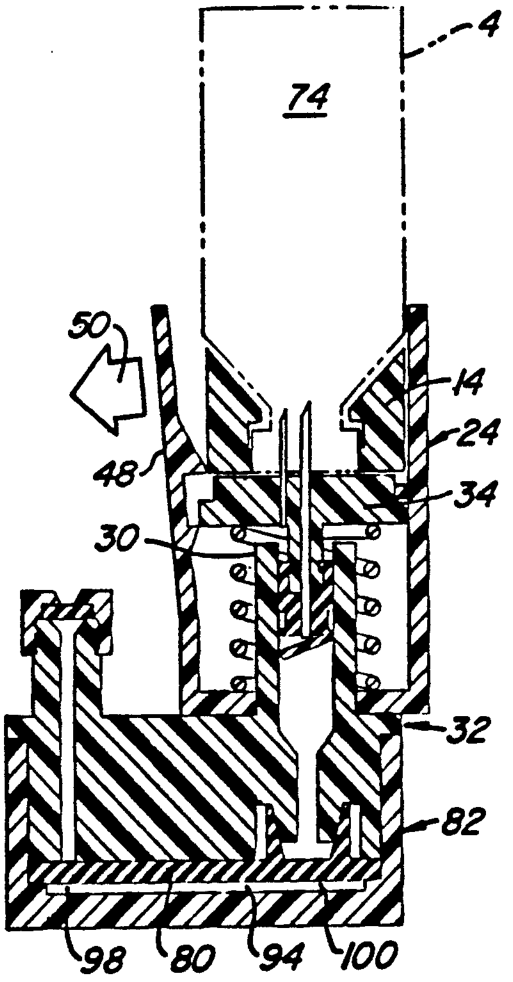
FIG. 5 illustrates the structure of FIG. 4 with the spikes fully penetrating the septum of the vial but prior to any axial movement of the piston within the cylinder.

Spike support 34 includes a pair of hollow, pointed spikes 54, 56 which are positioned to pierce the septum of vial 4 when the vial is mounted within split guide ring 24 as shown in FIGS. 4 and 5. Spikes 54 and 56 are both preferably of stainless steel. Spike 54 extends through a central bore within spike support 34 and through a cylindrical extension 58 of spike support 34. A combination piston/flapper valve 60, made of silicone rubber, is mounted to extension 58 and over the outer end 62 of liquid spike 54. Combination 60 includes a piston 64 sized to engage the cylinder wall 66 of cylinder 30. Combination 60 also includes a flapper valve element 68 which is hinged to piston 64 at position 70. The end of element 68 opposite position 70, indicated by reference numeral 72, touches cylinder wall 66 so that as piston 64 moves downwardly with respect to FIG. 3, element 68 is forced upwardly against the outer end 62 of liquid spike 54 thus sealing the liquid spike. When piston 30 moves in the opposite direction, that is upwardly with reference to FIG. 3, end 72 of element 68 also drags along wall 66 to move away from outer end 62 thus uncovering the outer end and permitting fluid communication between the interior 74 of vial 4 and interior or bore 76 of cylinder 30, which is defined by cylinder wall 66.

Figure 8:
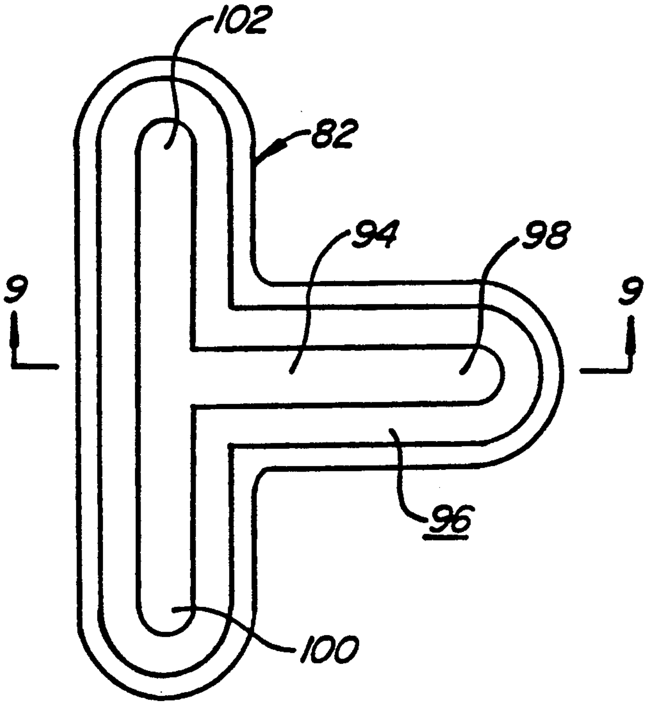
FIG. 8 is an enlarged top view of the manifold base of FIG. 2.
Figure 9:
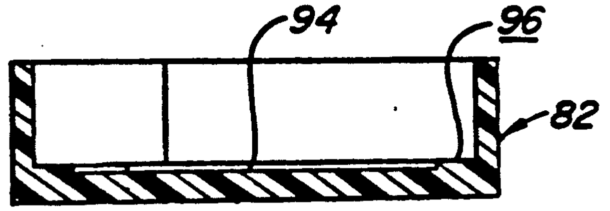
FIG. 9 is a cross-sectional view of the manifold base of FIG. 8 taken along line 9—9, the groove in the support surface of the manifold base being shown deeper than it is for purposes of illustration.
Figure 10:
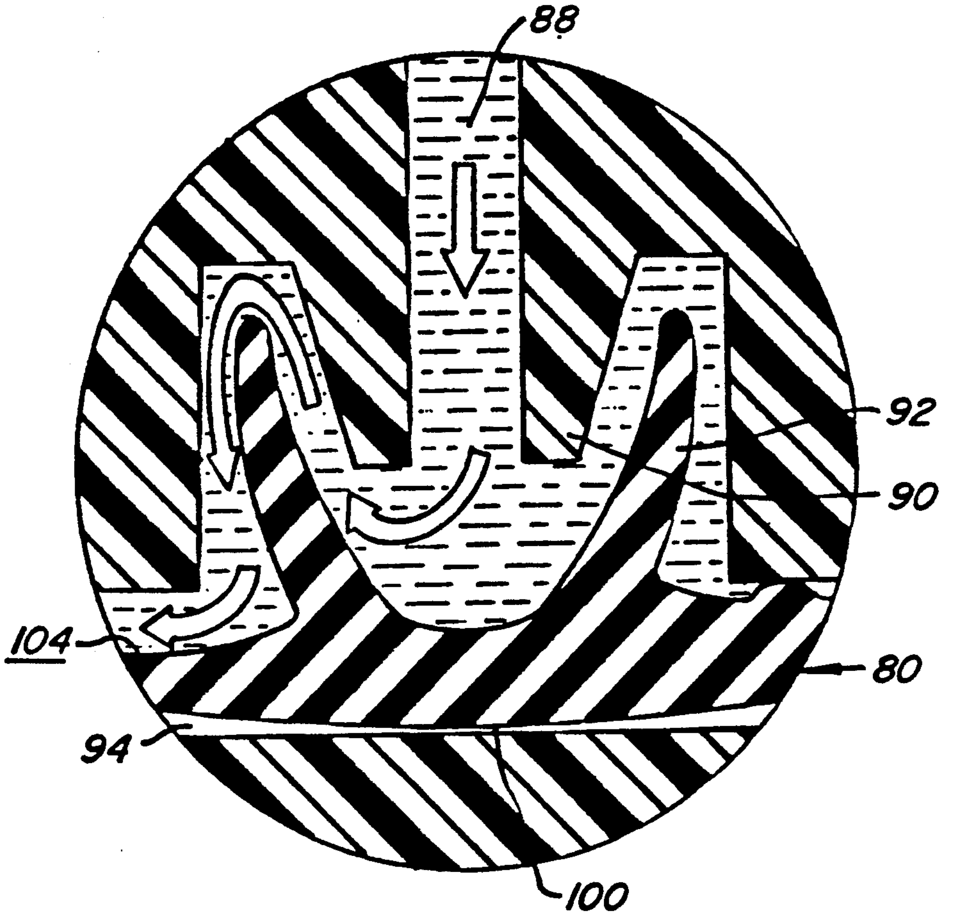
FIG. 10 illustrates in somewhat an exaggerated form the operation of the supplemental check valve formed by the tapered cup of the resilient manifold element and the externally tapered conical extension of the manifold cover.

Dispenser 2 also includes a manifold assembly 78. Manifold assembly 78 includes generally manifold cover 32, a resilient manifold element 80 and a manifold base 82. Resilient manifold element 80 is preferably made of silicone rubber while manifold base 82 is made of polycarbonate. Manifold assembly 78 defines a flow path extending from interior 76 of cylinder 30 to a needle cannula chamber 84 adjacent a needle cannula septum 86. Septum 86 is held in place by a threaded cap 87. Referring primarily to FIG. 3, interior 76 connects to a passageway 88 which passes through an externally conical element 90. Element 90 fits within an internally conically tapered cup-shaped extension 92 of resilient manifold element 80. As seen in FIGS. 8 and 9, manifold base 82 has a T-shaped groove 94 formed in its support surface 96. One end 98 of groove 94 is positioned beneath needle cannula chamber 84 while the other two ends 100, 102 are positioned below vials 4, 6. In the preferred embodiment, each arm of manifold base 82 is about 10 mm wide while groove 94 is about 0.25 mm deep and about 3 mm wide. The depth of groove 94 in the various figures has been exaggerated for purposes of illustration. The passage of the liquid medicine along the flow path will now be described with reference to FIGS. 6, 7 and 10.

Figure 6:
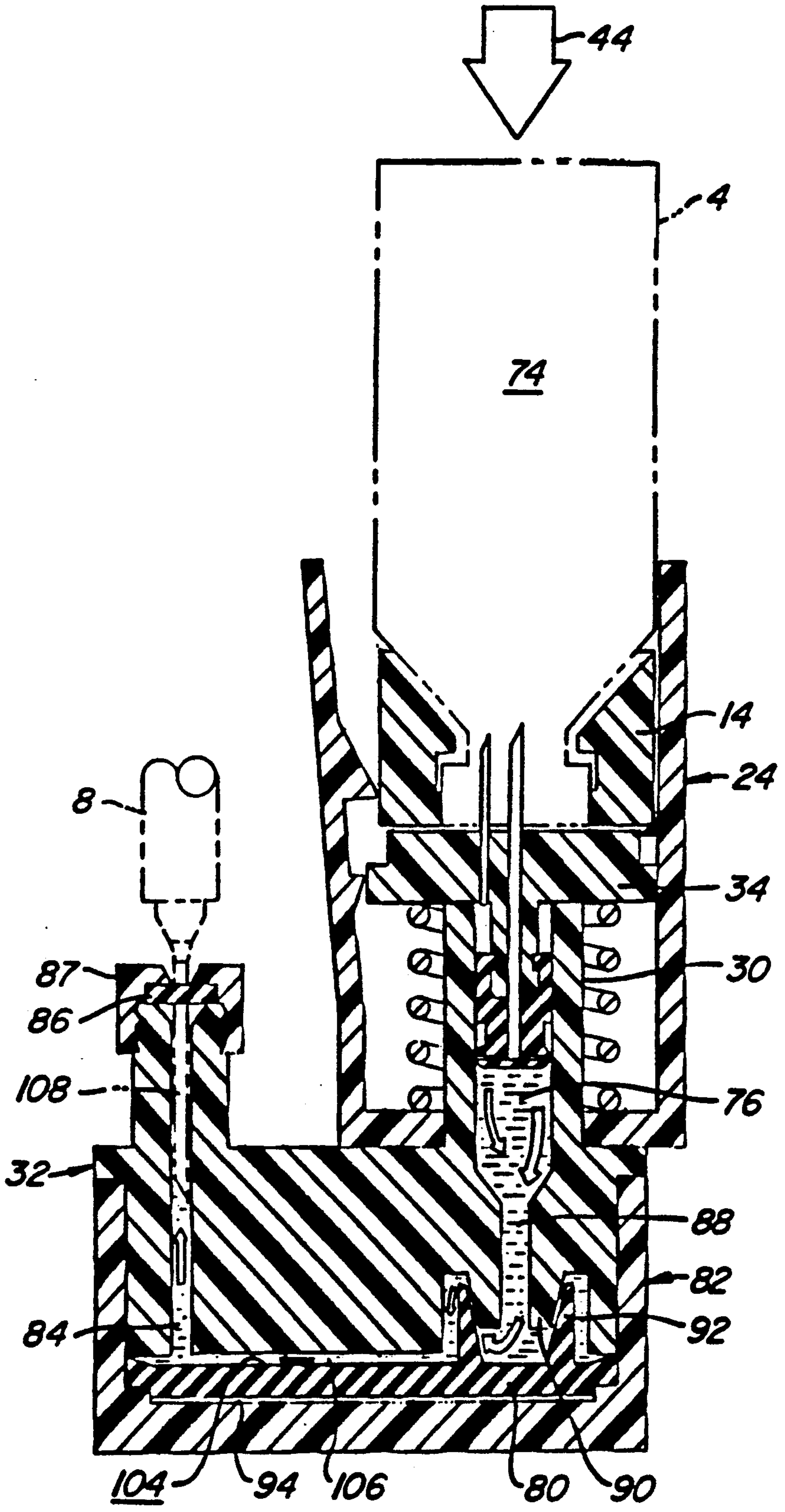
FIG. 6 illustrates the structure of FIG. 5, after the delivery stroke during which the piston moved to the delivery position, and illustrating the flow of fluid from the bore of the cylinder, along the flow path and to the needle cannula.
Figure 7:
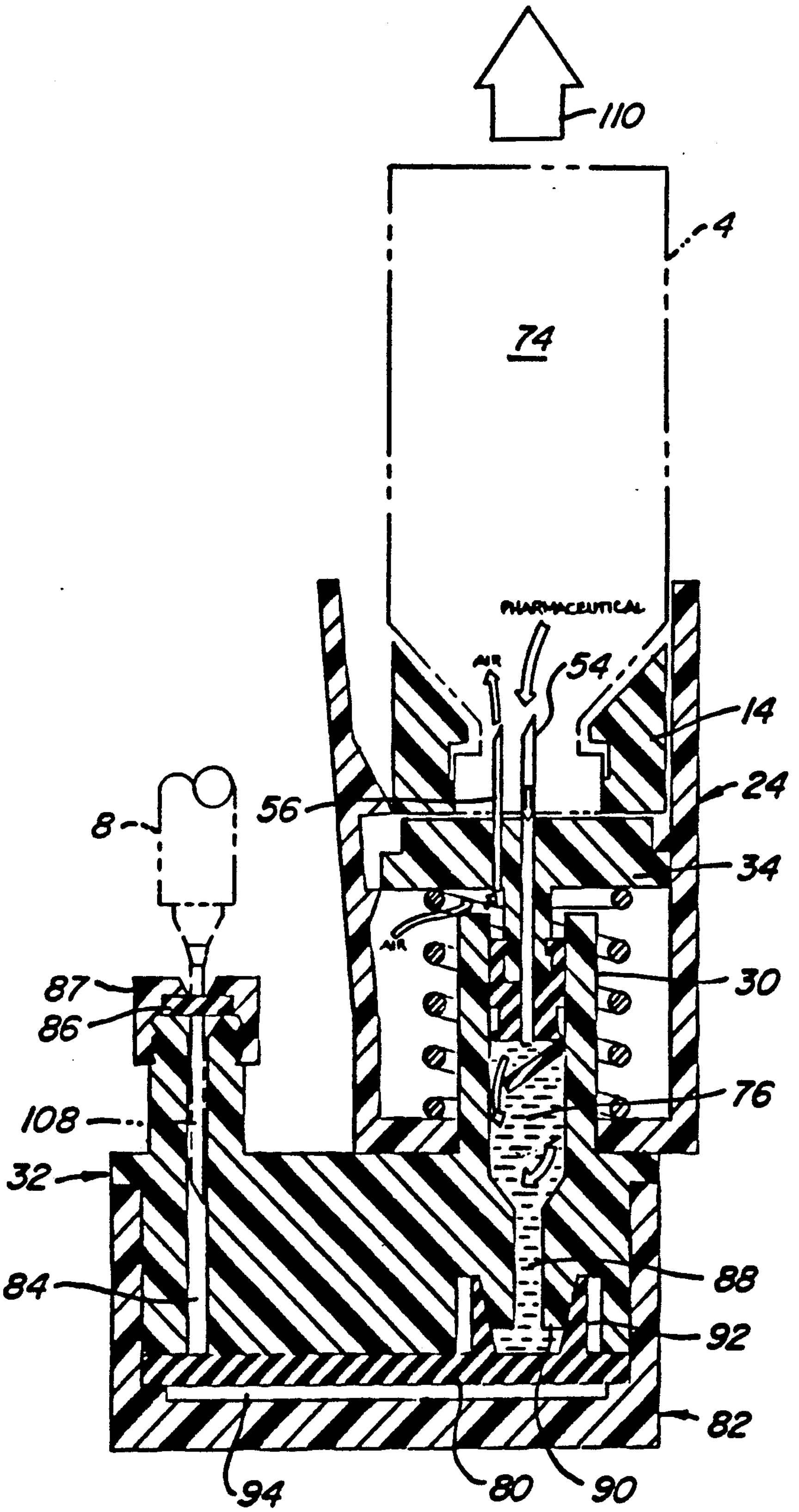
FIG. 7 illustrates the structure of FIG. 6 at the end of a replenish stroke, with the piston having moved to the replenish position, and the flow of fluid from the vial into the base of the cylinder as suggested by the arrows.

FIG. 6 shows the structure of FIG. 5 after the vial has been moved in the direction of arrow 44 from the replenish position of FIGS. 5 and 7 to the delivery position of FIG. 6 during a delivery stroke. During the delivery stroke illustrated in FIG. 6, the fluid, typically the liquid medication from within interior 74 of vial 4, is rather suddenly pressurized by the movement of piston 64. The sudden movement of liquid is resisted by the thin needle cannula 108. To accommodate the flow restriction created by having the liquid pass into syringe 8 through needle cannula 108, the flow path is configured to be resiliently expandable when subjected to pressurized fluid. This increased volume of the flow path is graphically illustrated when one compares FIGS. 6 and 7. During the delivery stroke, fluid in interior 76 is forced from interior 76 by the movement of piston 64 in the direction of arrow 44 causing the fluid to move along passageway 88. This pressurized fluid causes resilient manifold element 80 to bow downwardly, as suggested in exaggerated form in FIG. 10, into groove 94 and also causes cup-shaped extension 92 to bow outwardly permitting the fluid to move in the direction of the arrows of FIGS. 6 and 10. The fluid pressure also causes the remainder of resilient manifold element 80 to be deflected into groove 94, as can be seen by comparing FIGS. 5 and 6, so that the fluid moves along the flow path between the resilient surface 104 of element 80 and a bottom surface 106 of manifold cover 32. Thus, the region between surfaces 104, 106 along the flow path expands to accommodate the pressurization of the fluid caused by the delivery stroke.

FIG. 7 illustrates the replenish stroke during which the liquid medicine from the interior 74 of vial 4 is used to replace or replenish that which had been forced out of interior 76 of cylinder 30 during the delivery stroke. During movement of vial 4 in the direction of arrow 110, a low pressure region is formed in interior 76. This causes the supplemental valve created by conical element 90 and cup-shaped extension 92 to close. The movement of piston 64 in the direction of arrow 110 also causes end 72 of flapper valve element 68 to drag along cylinder wall 66 thus unsealing end 62 of liquid spike 54 to permit the flow of liquid medicine from interior 74, through liquid spike 54 and into interior 76 as suggested in FIG. 7. To permit this to occur, air spike 56 permits air to freely flow into interior 74 to replace the liquid pharmaceutical passing through liquid spike 54. Thus, interior 74 remains at atmospheric pressure at all times.

Figure 11:
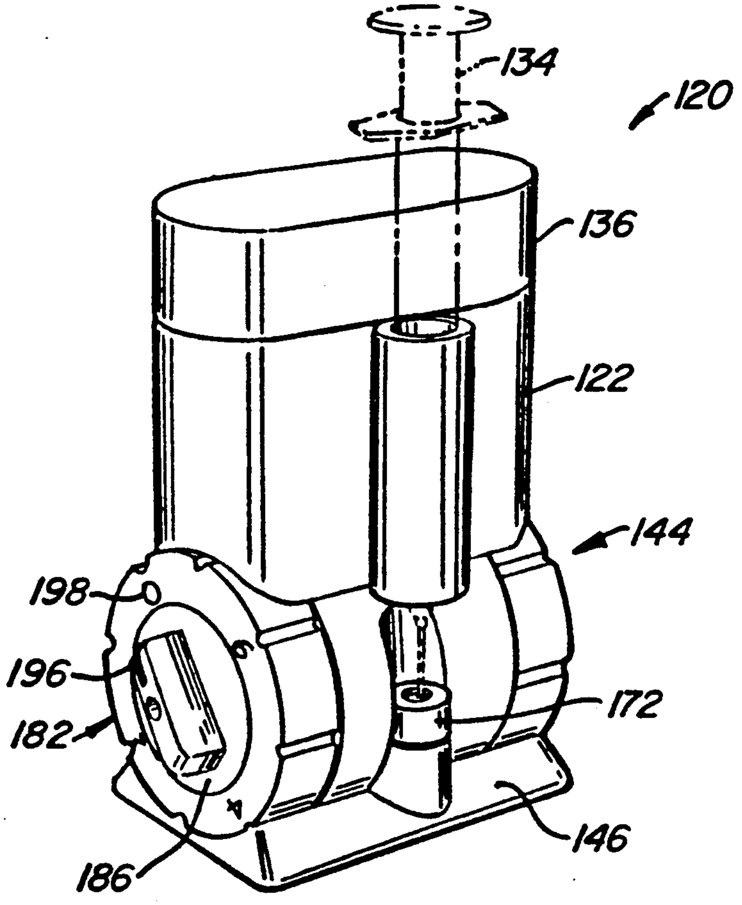
FIG. 11 is a perspective view of an alternative embodiment of the dispenser of FIG. 1 using a rotary peristaltic-type pump mechanism.
Figure 12:
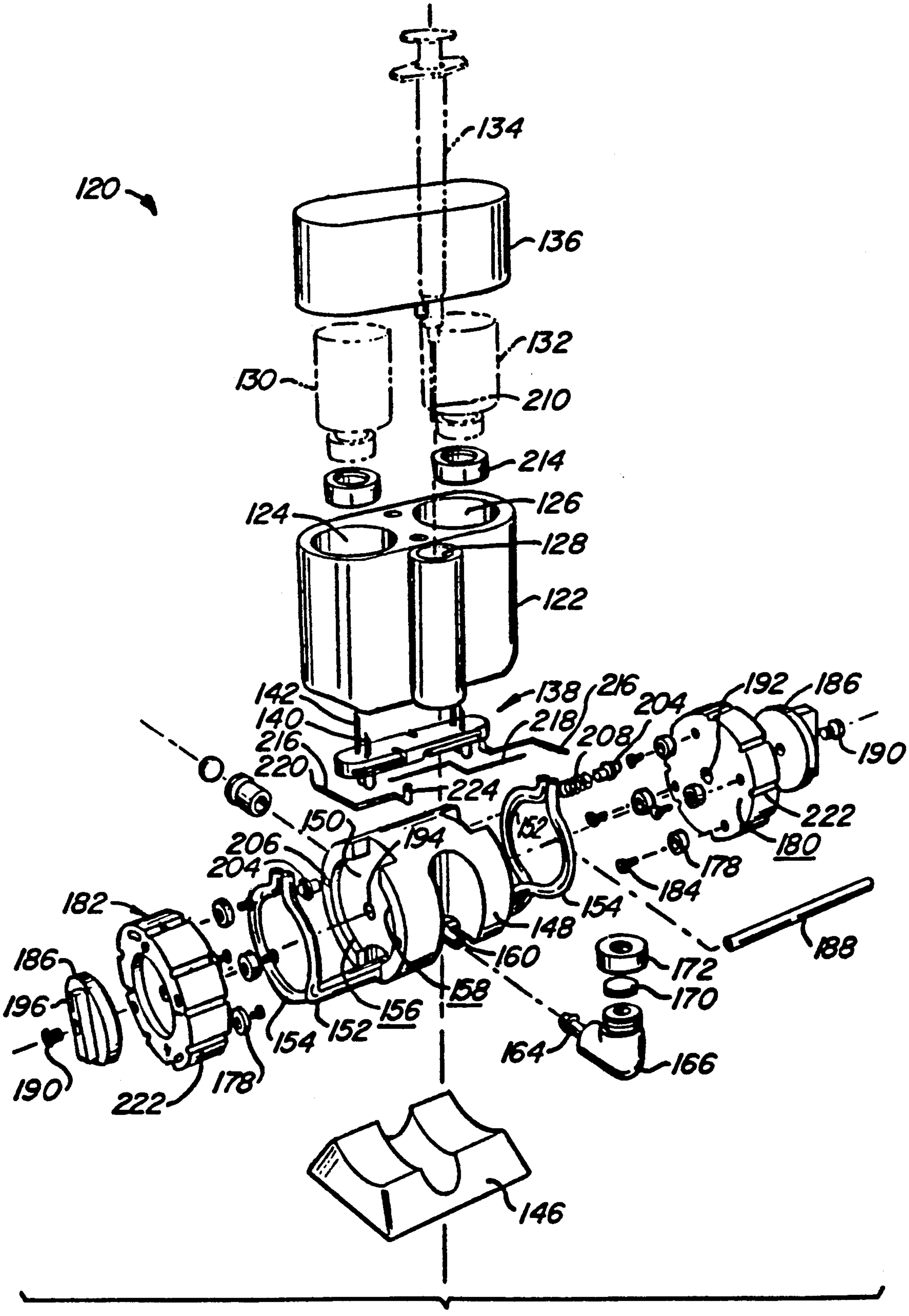
FIG. 12 is an exploded isometric view of the dispenser of FIG. 11 shown in conjunction with a pair of vials and a syringe in phantom lines.

FIGS. 11 and 12 illustrate an alternative embodiment of the invention which utilizes a peristaltic pump instead the reciprocal, piston and cylinder type of pump used with the embodiment of FIG. 1. Dispenser 120 includes a body 122 having cavities 124, 126 and 128 sized to accept vials 130, 132 and syringe 134. A lid 136 is mountable over cavities 124, 126 so to cover vials 130, 132. Dispenser 120 also includes a spike assembly 138 having two pairs of liquid and air spikes 140, 142, one pair for each of vials 130, 132. Dispenser 120 also includes a peristaltic pump assembly 144 secured to body 122 and resting on a base 146.

Figure 14:
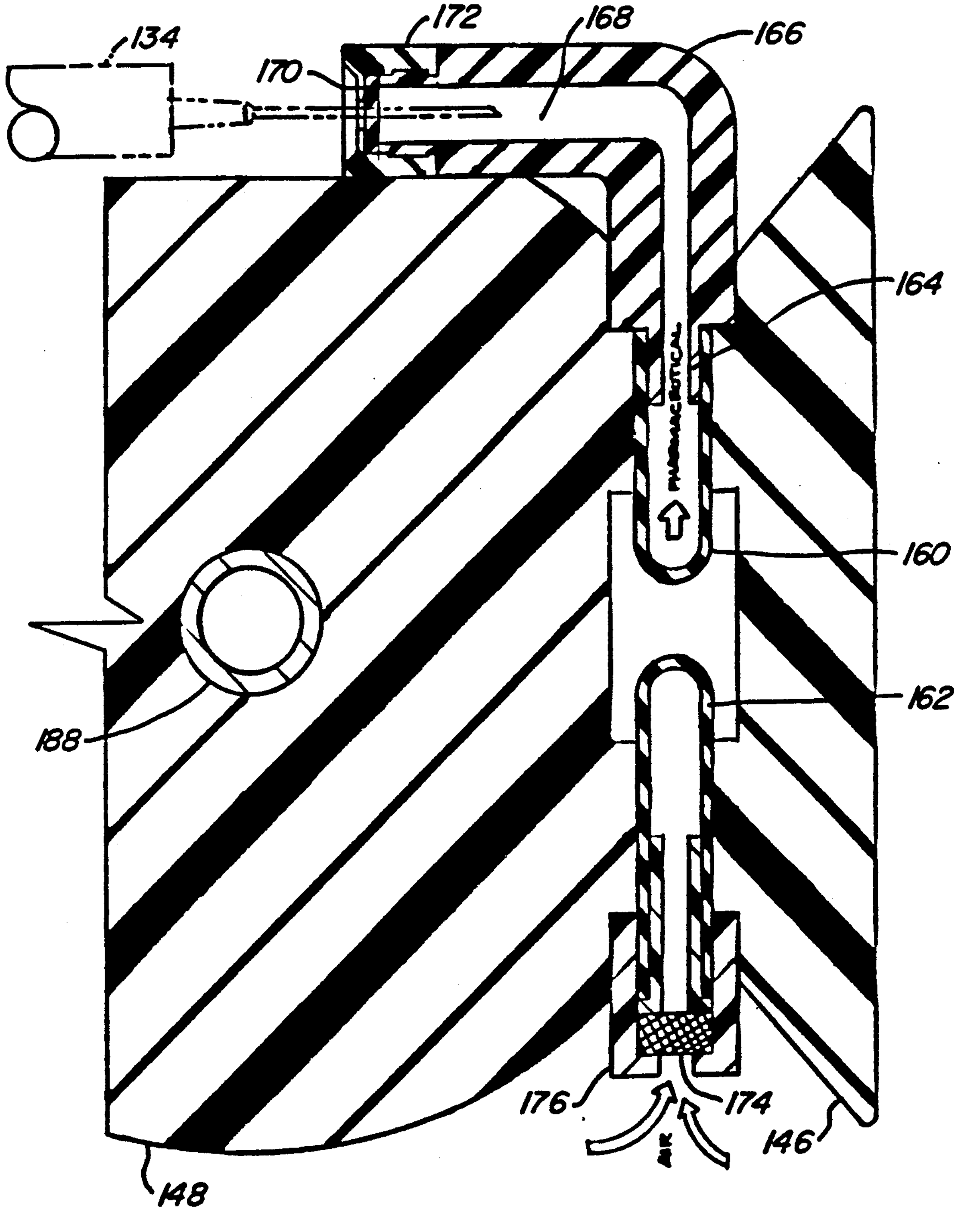
FIG. 14 is an enlarged cross-sectional view of a portion of the dispenser of FIG. 11 illustrating the air intake and the septum pierceable by the needle cannula of the syringe.

Pump assembly 144 includes a pump body 148 defining a pair of generally circular recesses 150. Flexible liquid and gas tubes 152, 154 are connected to liquid and gas spikes 140, 142 at their one ends and are positioned along the accurate inner surfaces 156, 158 which bound recess 150. The other ends of tubes 152, 154 terminate at T-connections 160, 162, shown in FIG. 14. Liquid T-connection 160 connects to a fitting 164 extending from an L-shaped element 166 defining a needle cannula chamber 168 bounded by a needle septum 170. Needle septum 170 is held in place by a threaded cap 172. Air T-connection 162 has an air filter 174 mounted at its end and secured in place by an air filter cap 176.

Figure 13:
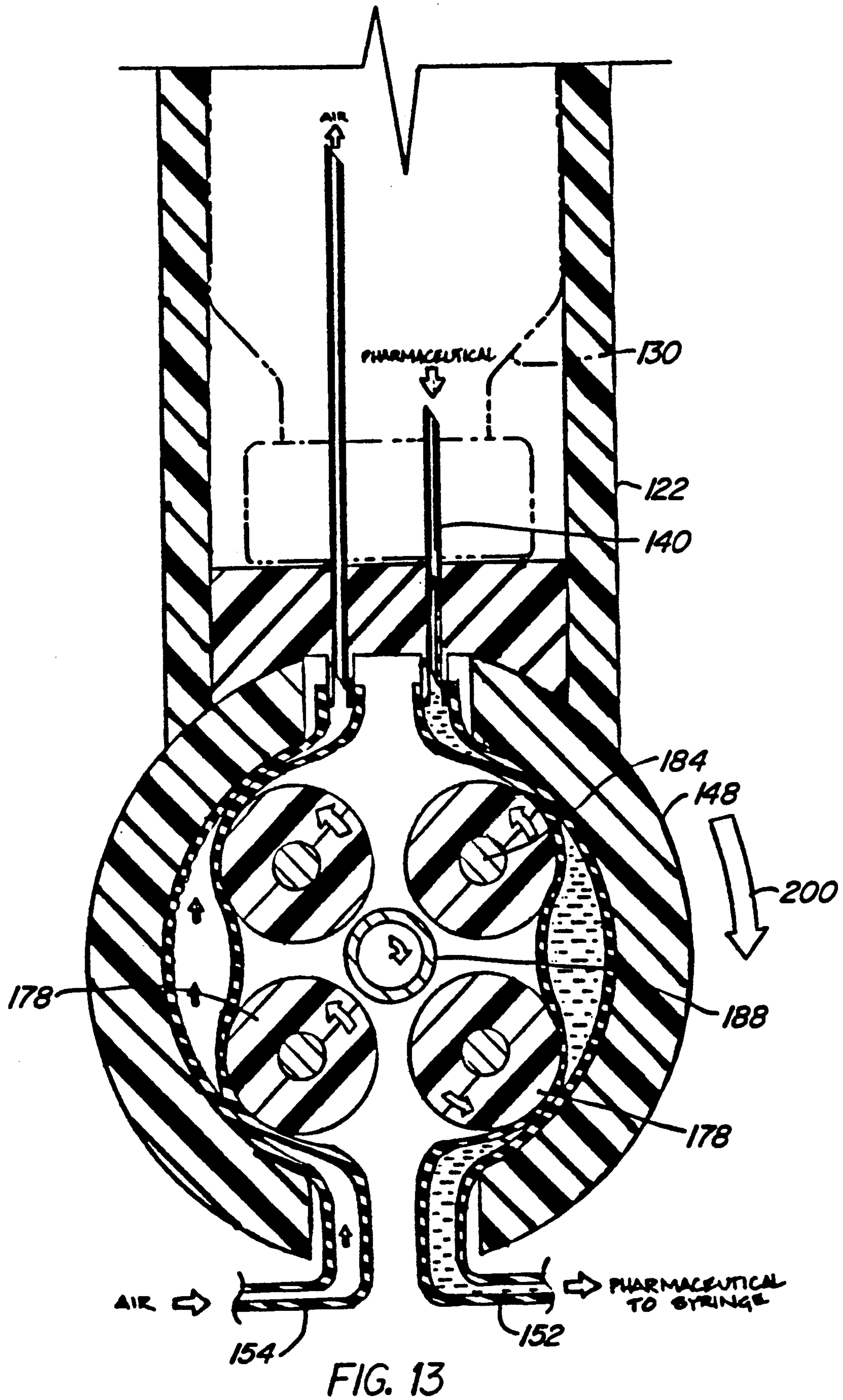
FIG. 13 is a partial cross-sectional view of the dispenser of FIG. 12 showing the pumping action of the peristaltic pump.

Four peristaltic rollers 178 are rotatably mounted to the inner surface 180 of a manually rotatable dial 182 by a number of screws 184. Dials 182 are held in place by knobs 186 which are fastened to the ends of an axle 188 by screws 190; screws 190 are threaded into complementary threaded holes at the ends of the axle. Axle 188 passes through holes 192 in dials 182 and also through a center bore 194 formed in body 148. There is sufficient frictional drag among axle 188, bore 194, knobs 186 and screws 190 so that rotation of dials 182 will not cause knobs 186 to rotate as well. Knobs 186 have zero indicators 196 which are oriented with dose indicator indicia 198, typically the zero indicia, at the beginning of use. As shown in FIG. 13, rotation of dials 182 in the direction of arrow 200 will cause rollers 178 to rotate about axle 188 and also about the screws 184 securing them to dial 182. This causes air to be forced into vial 130 and liquid to be forced out of vial 130 at the same rate so that the interior of the vial remains at atmospheric pressure. Using peristaltic pumps eliminates the need for check valves.

It is preferred that dials 182 move in only one direction. To facilitate this a ratchet mechanism is used. For example, a series of ramped depressions (not shown) can be formed in surface 180. These depressions are engaged by a pin 204 having one end housed within a bore 206 formed in body 148 and the other end pressing against surface 180 in position to engage the ramped depressions. Pins 204 are biased toward surfaces 180 by a common spring 208 housed within bore 206. Other anti-reverse mechanisms can be used as well.

Figure 13A:
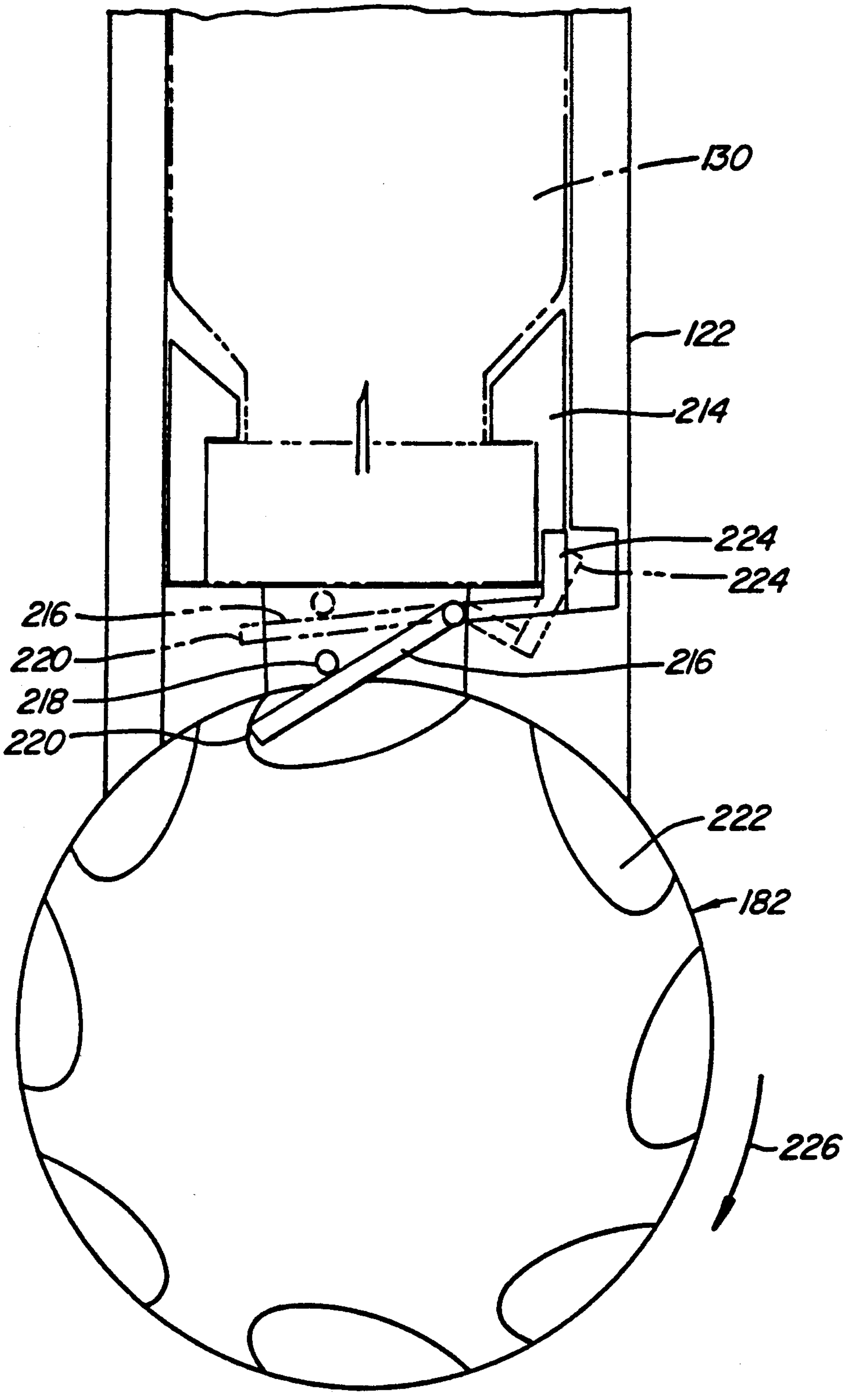
FIG. 13A is a simplified partial cross-sectional view of the dispenser of FIG. 12 showing the interlock mechanism which prevents the dials from being turned without a vial in place.

Split ring adaptors 214, see FIGS. 12 and 13A, are mounted over the ends of vials 130, 132. Ringer adaptors 214 operate to actuate interlock arms 216 when vials 130, 132 are fully within bores 124, 126 as in FIGS. 3 and 3A. Arms 216 are biased to the solid line position of FIG. 13A by a bent spring 218 so that the outer ends 220 of arms 216 engage grooves 222 formed in the outside of dials 182. When vials 130, 132 are in the positions of FIGS. 13, 13A, upstanding ends 224 of arms 216 are pushed downwardly to the dashed line position of FIG. 13A which lifts ends 220 out from groove .222 against the bias of spring 218. This prevents the rotation of dial 182 in the direction of arrow 226 unless a vial 130, 132 together with a proper adaptor ring 214 is fully mounted within body 122.

To operate dispenser 120, vials 130, 132 are placed into cavities 124, 126 so that their septums are pierced by spikes 140, 142. Lid 136 is then used to cover cavities 124, 126 and syringe 134 is mounted into syringe cavity 128 until the syringe's needle cannula 210 pierces septum 170. Knobs 186 are then rotated until the respective zero indicators 196 are aligned with zero dose indicia 198. Dials 182 are then rotated an appropriate amount according to the amount and proportion of each pharmaceutical. After the appropriate amount and proportion of the pharmaceuticals are pumped into syringe 134, the syringe is removed and the injection can be given.

In both embodiments there will be an initial amount of pharmaceutical which must be pumped from the vials along the flow path before any pharmaceutical is forced into the syringe. Thus, an initiation procedure must be followed to purge the air from the flow path. One way to do this is to force one or a combination of the liquid pharmaceuticals from the vials along the flow path. Once the liquid pharmaceutical begins to enter the syringe, the syringe could be withdrawn from the dispenser, the pharmaceutical expulsed from the syringe and the syringe reinserted into the dispenser. Subsequent pump actuation would cause accurate metering of the pharmaceuticals into the syringe. Alternatively, a bleed valve could be used adjacent the needle cannula septum to allow the air within the flow path to be expulsed. To ensure the proper proportion of the liquid pharmaceuticals are present in the flow path after the initialization, specialized procedures may be used. For example, if the desired mixture is equal parts of two pharmaceuticals, with the embodiment of FIG. 1 both vials 4, 6 could be pressed down, somewhat slowly, at the same time so that the fluid mixture within the flow path will be about equal parts of both liquid pharmaceuticals. In some cases the volume of liquid within the flow path is small enough not to matter insofar as proportions are concerned. Thus, any specialized procedures which may be used will depend upon the particular pharmaceuticals involved, the volume of the flow path and the need to have precise proportions. For example, a small variation in the proportions between two different types of insulin may not be significant.

FIGS. 15–20 are directed to an alternative embodiment of dispenser 2 of FIG. 1. Dispenser **2*a* is similar to dispenser 2 but can accommodate three medication containers in the form of cartridges as opposed to two vial type medication containers in the embodiment of FIG. 1. Also, dispenser 2*a* is constructed so that first cartridge 230 contains a diluent 231, second cartridge 232 contains a pharmaceutical component, in the preferred embodiment lyophilized pharmaceutical 233, while the third cartridge 234 contains a liquid pharmaceutical 235**.

Many of the components of dispensers 2, **2*a* are the same or related and have similar referencing numerals. Those aspects of dispenser 2*a* that are different from dispenser 2** are discussed below.

Body **16*a* has first, second and third cartridge guide bores 18*a*, 18*b*, 18*c* and a syringe guide bore 20*a* sized to fully contain the cartridges 230, 232, 234 and partially contained syringe 8. Body 16*a* has a pair of cutouts 236 adjacent bores 18*b*, 18*c* to permit the user visual access to the interiors of second and third cartridges 232, 234. The cutouts have clear sliders 238 which ride within cutouts 236. Sliders 238 can move within cutouts 236 but are snug enough within the cutout that once placed in position, the slider will stay in position until repositioned by the user. As shown best in FIG. 15, sliders 238 have a series of dose markings 240 including a zero marking 242. As will be discussed in more detail below, the amount of pharmaceutical within first or third cartridges 230, 234 which is forced into syringe 8 can be determined by first aligning zero marking 242 with a meniscus of the liquid pharmaceutical within container and then both counting the number of pump cycles and viewing the movement of the meniscus within cartridges 232, 234 along markings 240**.

Body **16*a* also includes a clear window 244 to allow the user to see the amount of diluent 231** within first cartridge 230. A syringe cutout 245 is formed along syringe guide bore 20a to allow the user visual access to the amount of medication forced into syringe 8.

Figure 15:
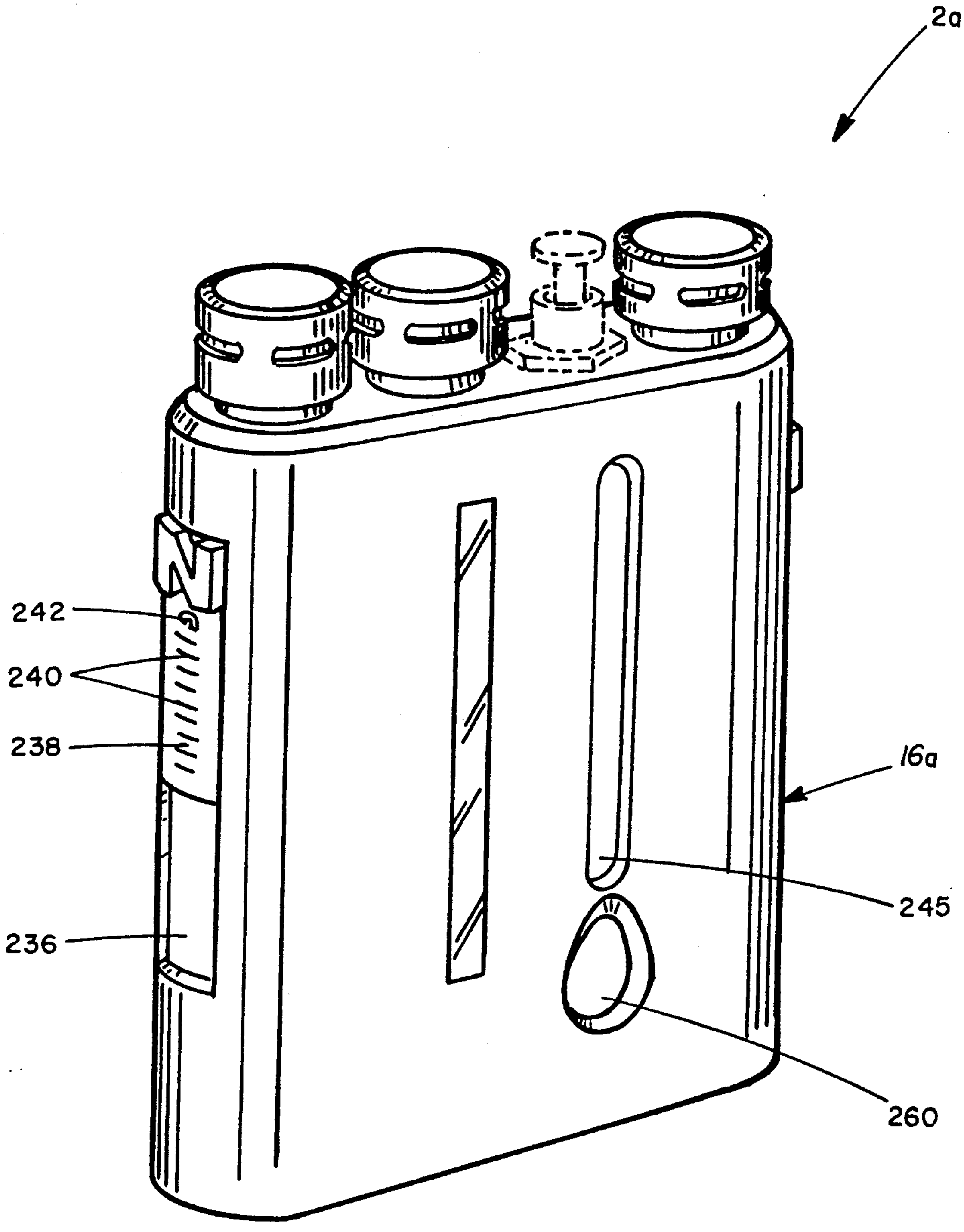
FIG. 15 is a perspective view of an alternative embodiment of the reciprocating pump multiple medication dispenser of FIG. 1 incorporating the ability to mix, and typically reconstitute, two pharmaceutical components prior to delivery of the mixed pharmaceutical into the syringe alone or in conjunction with another pharmaceutical.
Figure 16:
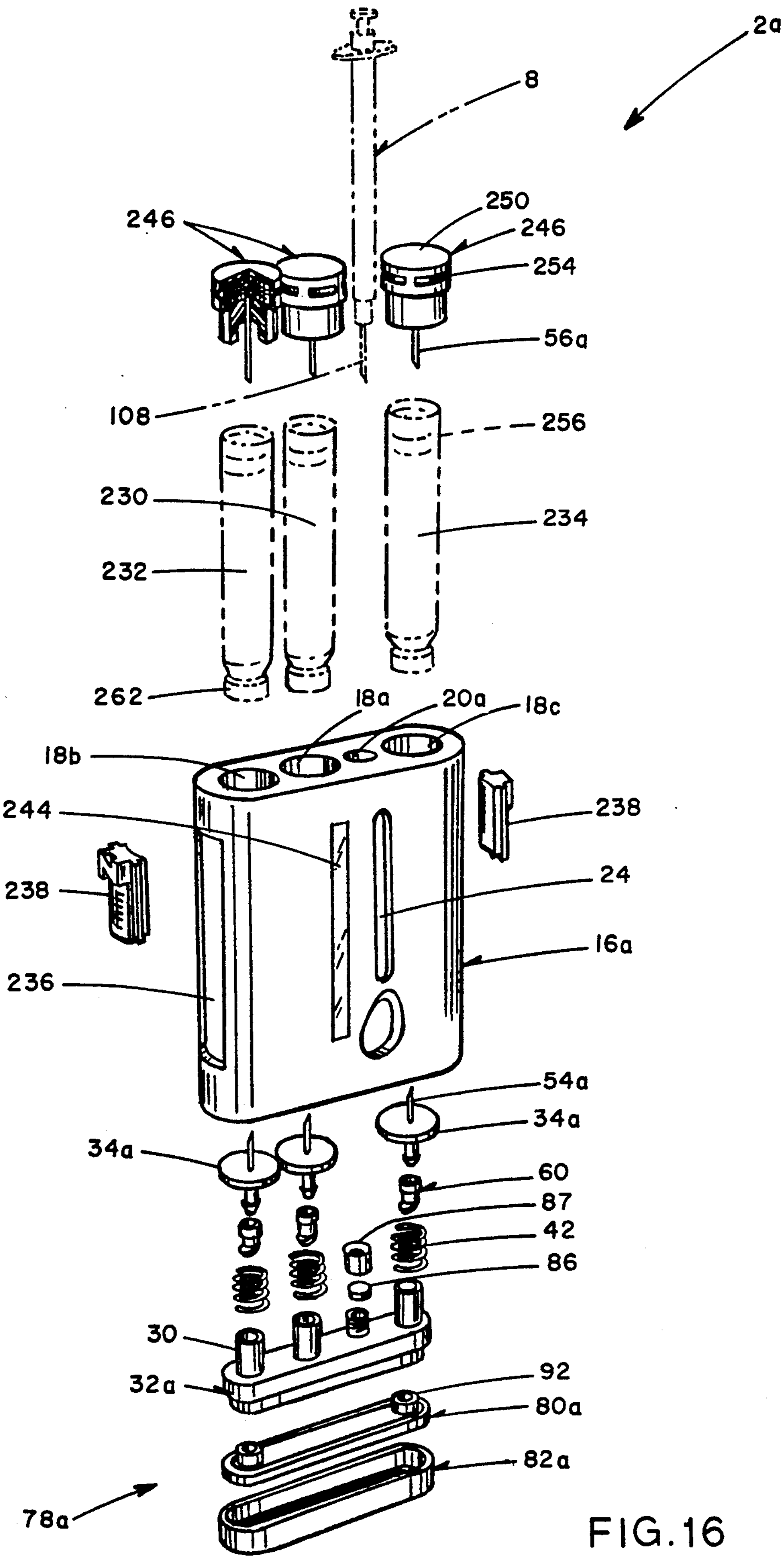
FIG. 16 is an exploded isometric view of the dispenser of FIG. 15.
Figure 17:
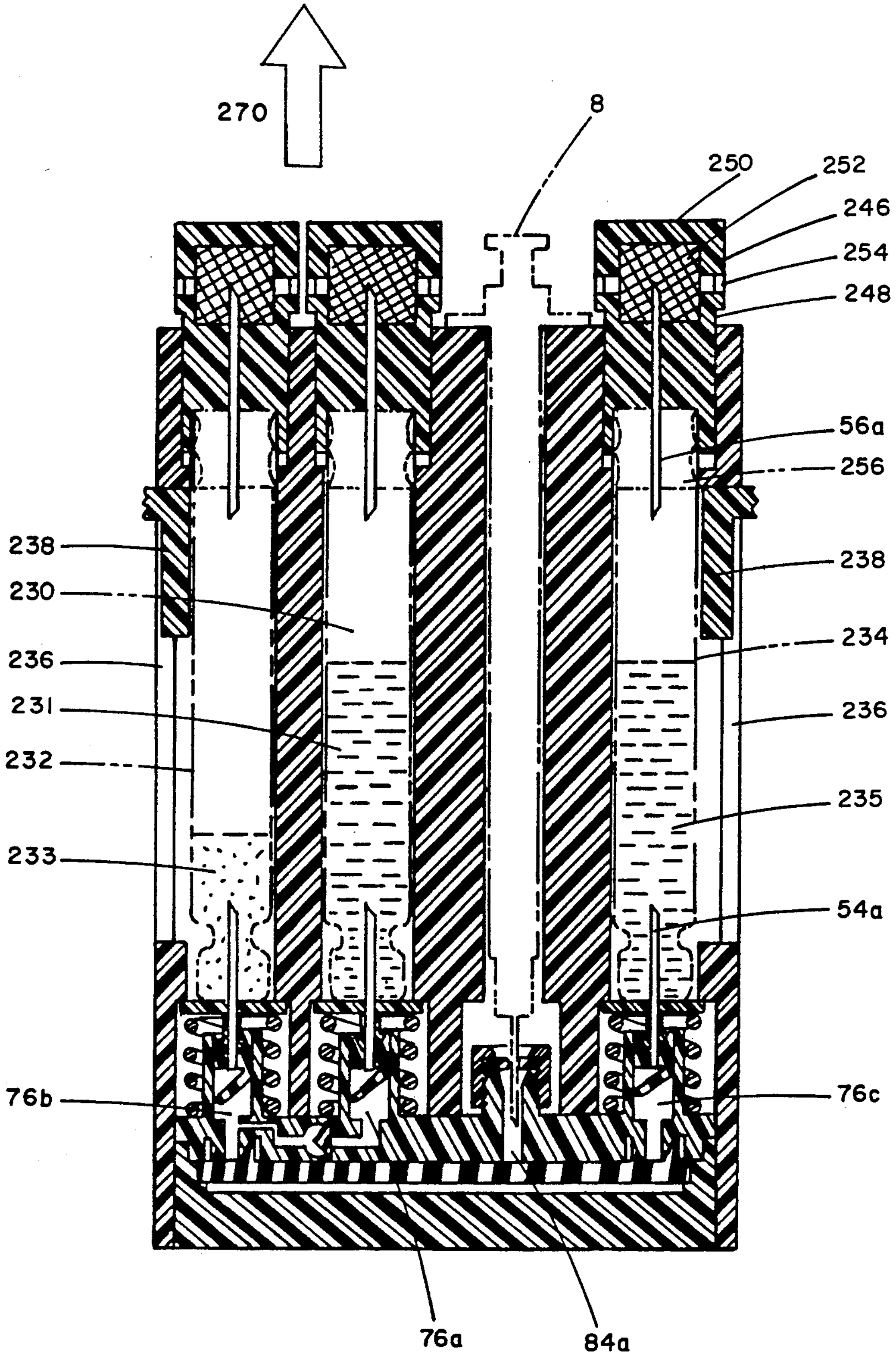
FIG. 17 is a cross-sectional view of the dispenser of FIG. 15 shown in the pre-use, as-delivered condition with a first cartridge containing a diluent, a second cartridge containing a lyophilized pharmaceutical component and a third cartridge containing a liquid pharmaceutical.

Prior to use dispenser 2a comes in the configuration of FIG. 15 but without cartridges 230, 232, 234 mounted therein. Dispenser 2a includes three gas spike assemblies 246. Each gas spike assembly 246 includes a generally cylindrical body 248 having a hollow, enlarged upper end 250. Gas spike 56a has its outer end exposed and its inner end positioned within the interior 252 of enlarged upper end 250 of spike assembly 246. Interior 252 is filled with a loose air filter material, such as cotton. Air flows into interior 252 through a set of air ports 254 extending around the periphery of enlarged upper end 250.

Figure 20:
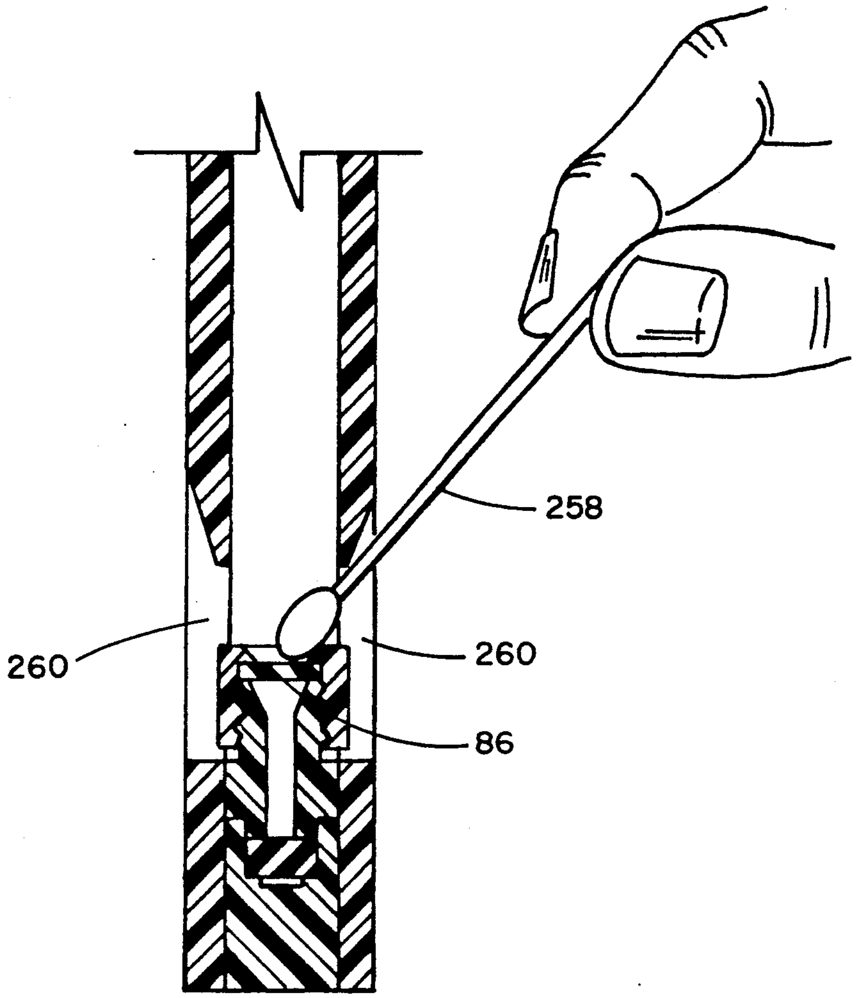
FIG. 20 is a transverse cross-sectional view of FIG. 15 showing a user swabbing a septum through an access opening in the body prior to piercing the septum with needle cannula of a syringe.

To mount cartridges 230, 232, 234 within bodies 16a, gas spike assemblies 246 are removed from cartridge guide bores 18a, 18b, 18c and cartridges 230, 232, 234 are mounted to the gas spike assemblies 246 by inserting gas spikes 56a through the pierceable, elastomeric piston 256 of each of cartridges 230, 232, 234. The combined cartridge/gas spike assembly is then mounted within the appropriate cartridge guide bore 18a, 18b, 18c. Septum 86 is cleaned using a swab 258 inserted through an access port 260 formed in body 16a as shown in FIG. 20.

Upon mounting the cartridge/gas spike assembly combination into body 16a, the septum ends 262 of the cartridges pass over liquid spikes 54a as the liquid spikes pass through the septums of the cartridges. At this point the interiors of the cartridges have two spikes, liquid spike 54a and gas spike 56a opening into the interior of the cartridges. Reciprocal movement of spike assembly 246 mounted to third cartridge 234 during its delivery and return strokes, which are down and up in the figures, causes pharmaceutical 235 to flow from the interior of cartridge 234, into bore 76c, past cup-shaped extension 92 between resilient manifold element 80a and manifold cover 32a, into needle cannula chamber 84a, through needle cannula 108 and into syringe 8. This occurs in the same basic manner for fluid flow from cartridge 232 into the syringe 8 and for the embodiment of FIGS. 1-10.

Figure 18:
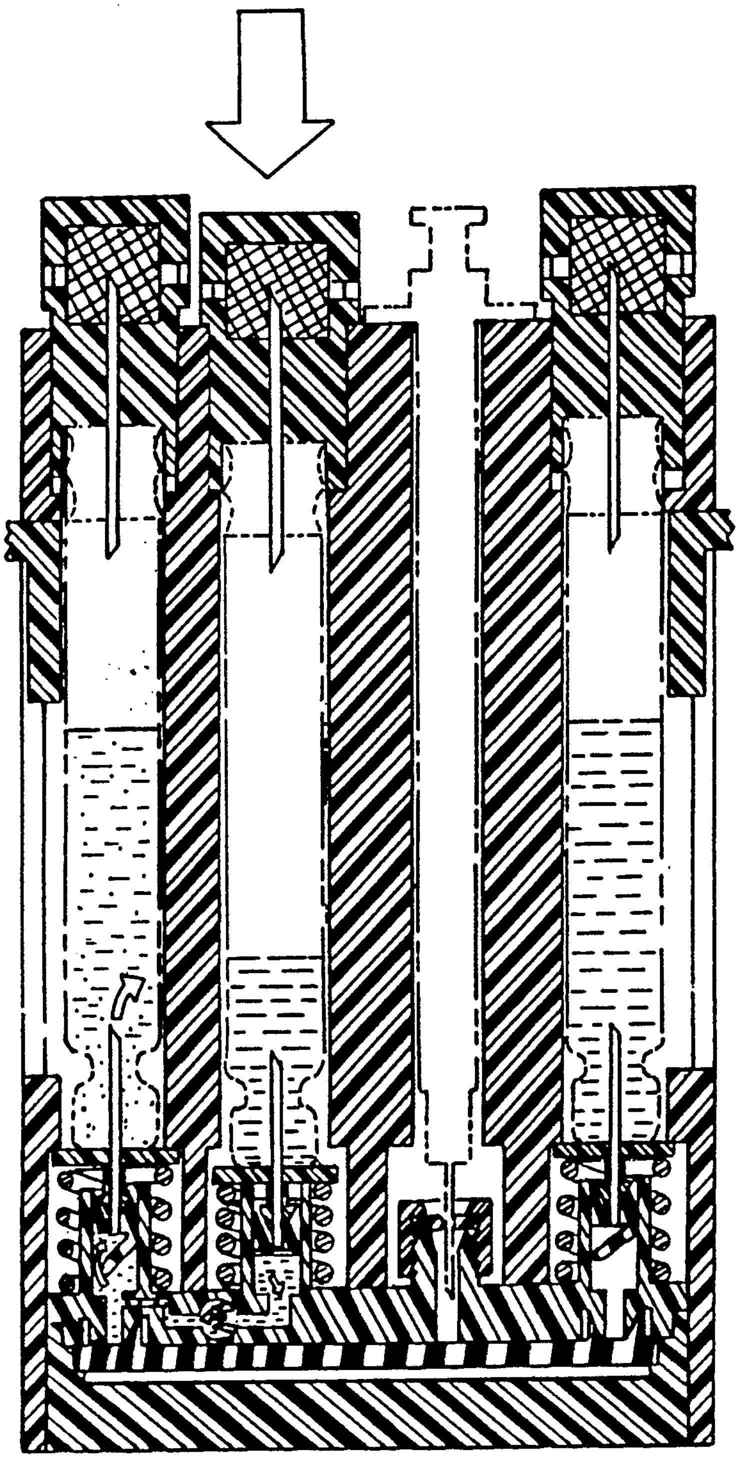
FIG. 18 shows the dispenser of FIG. 17 at the end of a delivery stroke, following several delivery strokes from the condition of FIG. 17, of the first cartridge thus driving the diluent from the cartridge into the second cartridge where the diluent mixes with and reconstitutes the lyophilized pharmaceutical component.
Figure 18A:
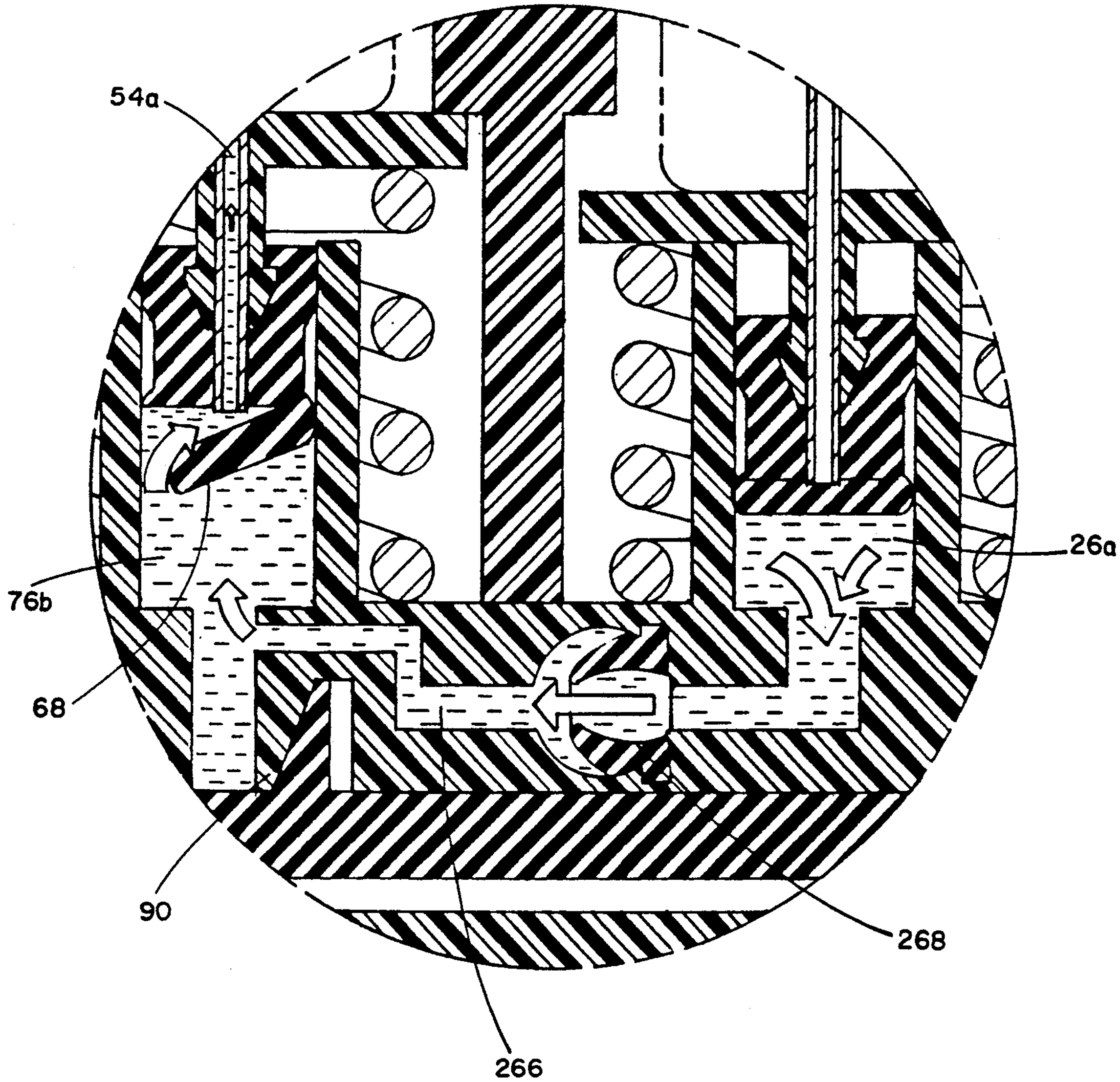
FIG. 18A is an enlarged view of a portion of the dispenser of FIG. 18 illustrating the fluid flow from the interior or bore of the cylinder associated with the first cartridge, along a passageway connecting the cylinders associated with the first and second cartridges, past a check valve positioned along a passageway, past a flapper valve element, through the liquid spike and into the second cartridge.

The main distinction between the two embodiments of FIGS. 1-10 and 15-20 relates to the ability of dispenser 2a to transfer the contents of cartridge 230 into cartridge 232, thus mixing with the contents of cartridge 232, before driving the mixture into syringe 8. Manifold cover 32a, as shown best in FIGS. 18A and 19A, defines a passageway 266 between bore 76a and bore 76b. A check valve 268 is positioned along passageway 266 to permit fluid to flow from bore 76a into bore 76b but not in the reverse direction. Thus, during a delivery stroke of cartridge 230, diluent 231 passes from bore 76a, through passageway 266, past check valve 268 and into bore 76b. At this point the diluent can either pass up through liquid spike 54a entering into second cartridge 232 or deflect resilient manifold 80a downwardly thus forcing cup-shaped element 92 away from conical element 90. However, the flow of the liquid diluent is substantially unrestricted past flapper valve element 68, through liquid spike 54a and into second cartridge 232 so that is the direction of travel of the diluent.

Figure 19:
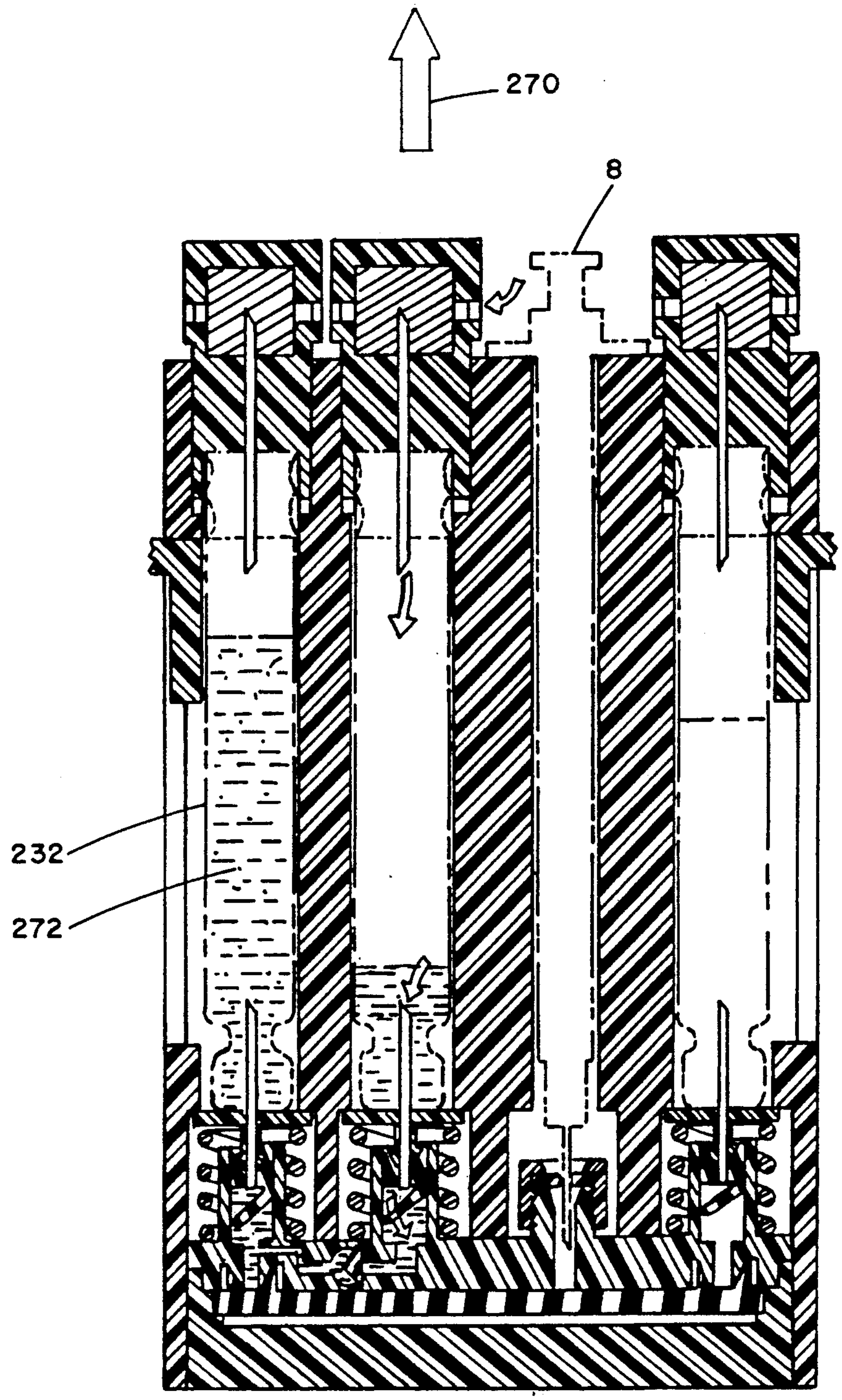
FIG. 19 illustrates the dispenser of FIG. 18 at the end of a replenish stroke of the first cartridge.
Figure 19A:
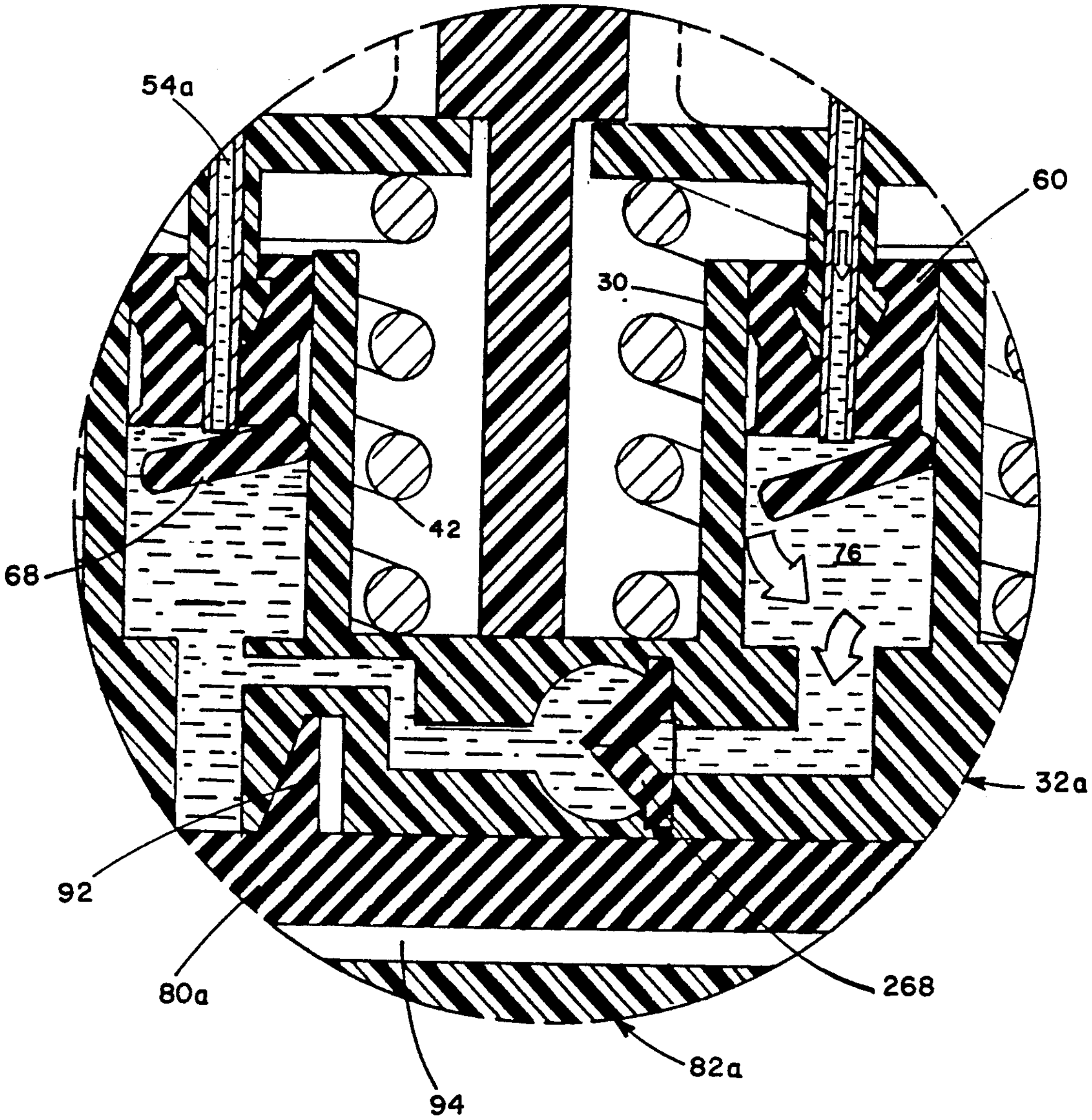
FIG. 19A illustrates an enlarged view of a portion of the dispenser of FIG. 19 illustrating the flow of liquid from the first cartridge, through the liquid spike, past the flapper valve element and into the interior of the cylinder associated with the first cartridge.

As can be seen in FIG. 19A, during the replenish stroke of first cartridge 230, that is when the first cartridge moves upwardly in the direction in arrow 270, diluent 231 goes into bore 76a thus replenishing the supply of the diluent in the bore as combination piston/flapper valve 60 moves upwardly. However, during this stroke check valve 268 remains closed so that liquid downstream of check valve 268 does not get pulled back into bore 76a. Once diluent 231 has been transferred into second cartridge 232 to form a mixed pharmaceutical 272, second cartridge 232 can be actuated or pumped to drive the mixed pharmaceutical from the second cartridge into syringe 8. Backflow into first cartridge 230 during this process is prevented by check valve 268.

This third embodiment has been described with reference to a diluent 231 and a lyophilized pharmaceutical component 233 which are combined and mixed to form a mixed pharmaceutical 272. However, lyophilized pharmaceutical component 233 could be replaced by a liquid pharmaceutical component. Diluent 231 could be replaced by a clinically active liquid pharmaceutical component. Accordingly, as used in this application, a pharmaceutical component can be an active component, such as a diluent 231, a lyophilized pharmaceutical component or a liquid pharmaceutical. A diluent can be mixed with a lyophilized, or other non-liquid, pharmaceutical or a liquid pharmaceutical. Likewise, both first and second cartridges 230, 232 could contain two clinically active pharmaceutical components.

Figure 21:
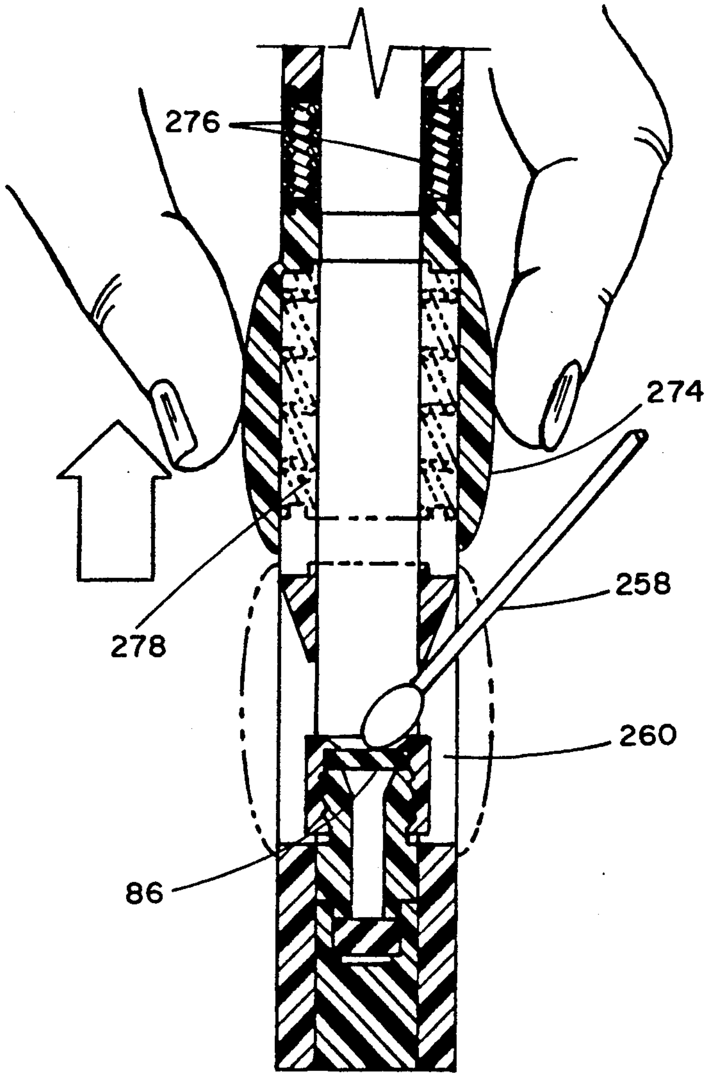
FIG. 21 shows an alternative embodiment of the invention in a view similar to that of FIG. 20 in which the user lifts a spring-biased cover, which normally covers the access opening, while swabbing the septum.

FIG. 21 illustrates an alternative embodiment of the invention in which access ports 260 are normally sealed by a two-sided cover 274. Cover 274 is biased to its closed (dashed-line) position by a pair of springs 276. Springs 276 are captured within openings 278 formed in body 16a in the region of the syringe cut-outs 245 of dispenser 2a. Therefore, septum 86 is exposed through ports 260 for cleaning.

Other modifications and variations can be made to the disclosed embodiments without departing from the subject of the invention as defined in the following claims. For example, the invention can be carried out using one or more than three pharmaceutical containers. Also, the same medication can be used in more than one of the containers. Gas spikes 56a could be used to pierce the septums of the cartridges in a manner similar to that used in the FIG. 1-10 embodiment. Receptacles other than a syringe, such as a needless injector or an IV bags could be used to accept the pharmaceuticals from the cartridge or vials. In such a case, a fluid connection other than a needle cannula 108 piercing a septum 86 could be used.

What is claimed is:

1. A multiple medication dispenser, for use with first and second containers containing first and second liquid medications and a syringe of the type including a needle cannula, a barrel and a plunger, the dispenser comprising:

a body to which the first and second containers and the syringe are mountable;

first and second dual port means for providing first and second gas and liquid ports into the interiors of the first and second containers;

first means for substantially simultaneously pumping a first gas into the first container through the first gas port and the first liquid medication from the first container through the first liquid port;

second means for substantially simultaneously pumping a second gas into the second container through the second gas port and the second liquid medication from the second container through the second liquid port;

means for fluidly directing the first and second liquid medications from the first and second pumping means to the needle cannula;

whereby the first and second liquid medications are pumped from the first and second containers by the first and second pumping means, through the needle cannula and into the syringe.

2. A medication dispenser, for use with a first container containing a first, liquid pharmaceutical, a second container containing a second pharmaceutical and a syringe of the type including a needle cannula, a barrel and a plunger, the dispenser comprising:

a body to which the containers and the syringe are mountable;

dual port means for providing first and second gas and liquid ports into the interiors of the first and second containers;

a first passageway fluidly connecting the first and second liquid ports to permit fluid flow from the first container to the second container but not flow in the reverse direction;

first means for pumping the first liquid pharmaceutical into the second container through the first and second liquid ports along the first passageway so the pumped first pharmaceutical mixes with the second pharmaceutical in the second container to create a first mixed liquid pharmaceutical while gasses pass into the first container and out of the second container through the first and second gas ports, respectively;

second means for pumping the first mixed liquid pharmaceutical from the second container through the second liquid port while replacing the first mixed pharmaceutical with gas which passes into the second container through the second gas port; and means for fluidly directing the first mixed pharmaceutical from the second liquid port to the needle cannula;

whereby the mixed pharmaceutical is pumped from the second container by the second pumping means, through the needle cannula and into the syringe.

3. The dispenser of claim 2 wherein the body includes cavities for housing the container and the syringe.

4. The dispenser of claim 2 wherein the dual port means includes a septum-pierceable, hollow liquid spike and a piston-pierceable, hollow gas spike.

5. The dispenser of claim 2 further comprising means for visually indicating the amount of the mixed pharmaceutical pumped into the syringe.

6. The dispenser of claim 5 wherein the first and second pumping means include means for preventing the pumping of liquid from the second container into the first container.

7. The dispenser of claim 2 wherein the fluidly directly means includes a septum mounted to the body and pierceable by the needle cannula.

8. The dispenser of claim 2 further comprising a gas filter coupled to the gas port.

9. The dispenser of claim 8 wherein the gas filter is coupled to the ambient atmosphere.

10. The dispenser of claim 2 wherein the first pumping means includes a piston and cylinder assembly.

11. The dispenser of claim 10 wherein the first pumping means is actuated by reciprocal movement of the first container.

12. The dispenser of claim 11 wherein the piston and cylinder assembly includes a cylinder and a piston, coupled to the first container, for reciprocal movement with the first container within the cylinder between a delivery position and a replenish position, the cylinder having a cylinder wall.

13. The dispenser of claim 12 wherein the first pumping means includes a check valve fluidly coupling the container and the cylinder.

14. The dispenser of claim 13 wherein:

the check valve includes a flapper element which frictionally engages the cylinder wall as the piston moves between the distal position and the proximal position;

the friction between the cylinder wall and the flapper element being sufficient and the flapper element constructed to cause the flapper element to seal the cylinder from the container and to fluidly couple the cylinder to the container when the piston moves towards the delivery position and towards the replenish position, respectively.

15. The dispenser of claim 2 wherein the fluidly directing means includes supplemental check valves which permit fluid flow from the second liquid port to the needle cannula but prevents fluid flow from the needle cannula to the second liquid port.

16. The dispenser of claim 2 wherein the fluidly directing means includes a resilient pathway element having a flow surface which can deflect according to a fluid pressure applied thereto.

17. The dispenser of claim 16 wherein the resilient pathway element includes an elastomeric material supported on a support surface containing a groove, the elastomeric material being deflectable into the groove thereby deflecting the flow surface.

18. The dispenser of claim 2 wherein the fluidly directing means includes accumulator means for providing a pressurized liquid accumulation region to accommodate any flow restriction created by the needle cannula.

19. A medication dispenser, for use with a first container containing a first, liquid pharmaceutical, a second container containing a second pharmaceutical, a third container containing a third, liquid pharmaceutical and a syringe of the type including a needle cannula, a barrel and a plunger, the dispenser comprising:

a body to which the containers and the syringe are mountable;

dual port means for providing first, second and third gas and liquid ports into the interiors of the first, second and third containers;

a first passageway fluidly connecting the first and second liquid ports to permit fluid flow from the first container to the second container but not flow in the reverse direction;

first means for pumping the first liquid pharmaceutical into the second container through the first and second liquid ports along the first passageway so the pumped first pharmaceutical mixes with the second pharmaceutical in the second container to create a first mixed liquid pharmaceutical while gasses pass into the first container and out of the second container through the first and second gas ports, respectively;

second means for pumping the first mixed liquid pharmaceutical from the second container through the second liquid port and the third, liquid pharmaceutical from the third container through the third liquid port while replacing the first mixed and third pharmaceuticals with gasses which pass into the second and third containers through the second and third gas ports; and means for fluidly directing the first mixed and third pharmaceuticals from the second and third liquid ports to the needle cannula;

whereby the mixed and third pharmaceuticals are pumped from the second and third containers by the second and third pumping means, through the needle cannula and into the syringe.

20. The dispenser of claim 19 further comprising means for visually indicating the amount of the mixed and third pharmaceuticals pumped into the syringe.

21. The dispenser of claim 19 wherein the first and second pumping means include means for preventing the pumping of liquid from the second container into the first or third containers and for preventing the pumping of liquid from the third container into the first or second containers.

22. The dispenser of claim 19 wherein the fluidly directing means includes supplemental check valves which permit fluid flow from the second and third liquid ports to the needle cannula but prevents fluid flow from the needle cannula to the second and third liquid ports.

* * * * *